US008410423B2

(12) United States Patent
Bartlett et al.

(10) Patent No.: US 8,410,423 B2
(45) Date of Patent: Apr. 2, 2013

(54) NUCLEAR GAUGES AND RELATED METHODS OF ASSEMBLY

(75) Inventors: James E. Bartlett, Cary, NC (US); Raffaello Verna, Creedmoor, NC (US); James D. Pratt, Jr., Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 785 days.

(21) Appl. No.: 12/348,841

(22) Filed: Jan. 5, 2009

(65) Prior Publication Data
US 2009/0250599 A1 Oct. 8, 2009

Related U.S. Application Data

(60) Provisional application No. 61/010,103, filed on Jan. 4, 2008, provisional application No. 61/010,022, filed on Jan. 4, 2008, provisional application No. 61/010,191, filed on Jan. 4, 2008.

(51) Int. Cl.
*G01V 5/08* (2006.01)
(52) U.S. Cl. .................. 250/269.1; 250/239; 250/269.3; 250/515.1
(58) Field of Classification Search ................ 250/269.1
See application file for complete search history.

(56) References Cited

U.S. PATENT DOCUMENTS

| | | | |
|---|---|---|---|
| 3,544,793 A | 12/1970 | Bless et al. | |
| 3,635,082 A | 1/1972 | Prellwitz et al. | |
| 3,794,843 A | 2/1974 | Chen | |
| 4,219,776 A | 8/1980 | Arulanandan | |
| 4,419,585 A * | 12/1983 | Strauss et al. ............. | 250/505.1 |
| 4,442,701 A | 4/1984 | Cowherd et al. | |
| 4,525,854 A | 6/1985 | Molbert et al. | |
| 4,587,623 A | 5/1986 | Regimand et al. | |
| 4,641,030 A | 2/1987 | Regimand | |
| 4,701,868 A | 10/1987 | Regimand | |
| 4,749,858 A | 6/1988 | Young | |
| 4,766,319 A | 8/1988 | Regimand | |
| 4,791,656 A | 12/1988 | Pratt, Jr. et al. | |
| 4,904,942 A | 2/1990 | Thompson | |

(Continued)

FOREIGN PATENT DOCUMENTS

CN ZL 200680040215.X 9/2011
EP 1 932 020 6/2008

(Continued)

OTHER PUBLICATIONS

First Office Action for Chinese Patent Application No. 200980107515.9 (Jan. 11, 2012).

(Continued)

*Primary Examiner* — David Porta
*Assistant Examiner* — Marcus Taningco
(74) *Attorney, Agent, or Firm* — Jenkins, Wilson, Taylor & Hunt, P.A.

(57) ABSTRACT

Nuclear gauges, their components and method for assembly and adjustment of the same are provided. The nuclear gauges are used in measuring the density and/or moisture of construction-related materials. The nuclear gauge can include a gauge housing having a vertical cavity therethrough and at least one radiation detector located within the housing. The nuclear gauge can include a vertically moveable source rod and a radiation source operatively positioned within a distal end of the source rod. The nuclear gauge can also include a radiation shield assembly.

46 Claims, 29 Drawing Sheets

U.S. PATENT DOCUMENTS

| | | | |
|---|---|---|---|
| 5,095,465 | A | 3/1992 | Stokoe, II |
| 5,333,502 | A | 8/1994 | Clark, Jr. et al. |
| 5,457,628 | A | 10/1995 | Theyanayagam |
| H1561 | H | 7/1996 | Thompson |
| 5,614,670 | A | 3/1997 | Nazarian et al. |
| 5,900,736 | A | 5/1999 | Sovik et al. |
| 5,923,726 | A | 7/1999 | Regimand |
| 6,050,725 | A | 4/2000 | Regimand |
| 6,272,434 | B1 | 8/2001 | Wisler et al. |
| 6,310,936 | B1 | 10/2001 | Troxler et al. |
| 6,369,381 | B1 | 4/2002 | Troxler et al. |
| 6,382,045 | B1 | 5/2002 | Wheeler |
| 6,393,921 | B1 | 5/2002 | Grimes et al. |
| 6,397,661 | B1 | 6/2002 | Grimes et al. |
| 6,400,161 | B1 | 6/2002 | Geisel |
| 6,411,087 | B1 | 6/2002 | Fan et al. |
| 6,414,497 | B1 | 7/2002 | Sovik et al. |
| 6,427,774 | B2 | 8/2002 | Thomas et al. |
| 6,442,232 | B2 | 8/2002 | Troxler et al. |
| 6,567,498 | B1 | 5/2003 | Troxler et al. |
| 6,604,432 | B1 | 8/2003 | Hamblen et al. |
| 6,677,763 | B2 | 1/2004 | Geisel |
| 6,803,771 | B2 | 10/2004 | Sovik et al. |
| 6,823,736 | B1 | 11/2004 | Brock et al. |
| 6,915,216 | B2 | 7/2005 | Troxler et al. |
| RE38,910 | E | 12/2005 | Troxler et al. |
| 6,980,929 | B2 | 12/2005 | Aronstam et al. |
| 7,040,145 | B2 | 5/2006 | Drnevich et al. |
| 7,042,801 | B1 | 5/2006 | Berg |
| 7,107,159 | B2 | 9/2006 | German |
| 7,132,662 | B2 | 11/2006 | Baldwin et al. |
| 7,219,024 | B2 | 5/2007 | Gamache et al. |
| 7,373,504 | B1 | 5/2008 | Belgaied et al. |
| 7,376,530 | B2 | 5/2008 | Bienvenu et al. |
| 7,569,810 | B1 | 8/2009 | Troxler et al. |
| 7,581,446 | B2 | 9/2009 | Troxler |
| 7,605,366 | B2 | 10/2009 | Dep et al. |
| 7,705,614 | B2 | 4/2010 | Troxler et al. |
| 7,820,960 | B2 | 10/2010 | Troxler |
| 7,872,222 | B1 | 1/2011 | Dep et al. |
| 7,928,360 | B2 | 4/2011 | Troxler |
| 8,011,248 | B2 | 9/2011 | Troxler |
| 8,071,937 | B2 | 12/2011 | Troxler |
| 8,164,048 | B2 | 4/2012 | Weger et al. |
| 2001/0055363 | A1 | 12/2001 | Troxler et al. |
| 2002/0149617 | A1 | 10/2002 | Becker |
| 2003/0038634 | A1 | 2/2003 | Strack |
| 2003/0141464 | A1 | 7/2003 | Weger et al. |
| 2003/0222662 | A1 | 12/2003 | Geisel |
| 2004/0073382 | A1 | 4/2004 | Troxler et al. |
| 2004/0095154 | A1 | 5/2004 | Lundstrom et al. |
| 2004/0260504 | A1 | 12/2004 | Bienvenu et al. |
| 2005/0150278 | A1 | 7/2005 | Troxler et al. |
| 2005/0253703 | A1 | 11/2005 | He et al. |
| 2005/0267700 | A1 | 12/2005 | Gamache et al. |
| 2007/0216573 | A1 | 9/2007 | Handermann et al. |
| 2009/0194676 | A1 | 8/2009 | Weger et al. |
| 2009/0274275 | A1 | 11/2009 | Bartlett et al. |
| 2009/0314090 | A1 | 12/2009 | Troxler |
| 2011/0035182 | A1 | 2/2011 | Troxler |
| 2011/0194672 | A1 | 8/2011 | Troxler |
| 2012/0056627 | A1 | 3/2012 | Troxler |
| 2012/0169456 | A1 | 7/2012 | Weger et al. |

FOREIGN PATENT DOCUMENTS

| | | |
|---|---|---|
| EP | 1 943 479 | 7/2008 |
| GB | 863886 | 3/1961 |
| GB | 1284295 | 8/1972 |
| WO | WO 02/03055 | 1/2002 |
| WO | WO 2007/027760 | 3/2007 |
| WO | WO 2007/027797 | 3/2007 |
| WO | WO 2009/089172 A2 | 7/2009 |

OTHER PUBLICATIONS

Notice of Allowance and Fee(s) Due for U.S. Appl. No. 12/348,821 (Dec. 23, 2011).

Restriction Requirement for U.S. Appl. No. 12/348,784 (Sep. 19, 2011).

Restriction Requirement for U.S. Appl. No. 12/348,821 (Sep. 6, 2011).

Commonly-assigned, co-pending U.S. Appl. No. 13/225,386 for "Methods, Systems, and Computer Program Products for Determining a Property of Construction Material," (Unpublished, filed Sep. 2, 2011).

First Office Action for Chinese Patent Application No. 200680040289.3 (Jul. 19, 2011).

Notification of Transmittal of International Preliminary Report on Patentability for International Application No. PCT/US06/33839 (Jul. 13, 2011).

Notice of Allowance and Fee(s) Due for U.S. Appl. No. 13/089,196 (Jun. 28, 2011).

Notice of Granting Patent Right for Invention for Chinese Patent Application No. 200680040215.X (May 25, 2011).

Notice of Allowance and Fee(s) Due for U.S. Appl. No. 12/551,241 (May 11, 2011).

Commonly-assigned, co-pending U.S. Appl. No. 13/089,196 for "Methods, Systems, and Computer Program Products for Measuring the Density of Material Including a Non-Nuclear Moisture Property Detector," (Unpublished, filed Apr. 18, 2011).

Supplementary European Search Report for European Patent No. 1932020 (Jan. 20, 2011).

Notice of Allowance and Fee(s) Due for U.S. Appl. No. 12/910,745 (Dec. 13, 2010).

Communication of European publication number and information on the application of Article 67(3) EPC for International Application No. PCT/US09/30136 (Sep. 15, 2010).

Non-Final Official Action for U.S. Appl. No. 12/551,241 (Sep. 8, 2010).

Notification of Transmittal of the International Preliminary Report on Patentability for International Application No. PCT/US09/30136 (Jul. 15, 2010).

Notice of Allowance and Fee(s) Due for U.S. Appl. No. 12/534,739 (Jun. 17, 2010).

Official Action for Chinese Patent Application No. 200680040215.X (Apr. 29, 2010).

Official Action for Chinese Patent Application No. 200680040215.X (Dec. 18, 2009).

Notification of Transmittal of the International Search Report and the Written Opinion of the International Searching Authority, or the Declaration for International Application No. PCT/US09/30136 (Jul. 15, 2009).

Notice of Allowance and Issue Fees(s) Due for U.S. Appl. No. 11/513,334 (Jun. 12, 2009).

Notice of Allowance and Issue Fees(s) Due for U.S. Appl. No. 11/512,732 (May 29, 2009).

Final Official Action for U.S. Appl. No. 11/513,334 (Oct. 30, 2008).

Official Action for U.S. Appl. No. 11/512,732 (Sep. 11, 2008).

Notification of Transmittal of International Preliminary Report on Patentability for International Application No. PCT/US2006/033898 (Jun. 23, 2008).

Notification of Transmittal of the International Search Report and The Written Opinion of the International Searching Authority, or the Declaration for International Application No. PCT/US2006/033839 (May 29, 2008).

Notification Concerning Trasmittal of International Preliminary Report on Patentability for International Application No. PCT/US2006/033898 (March 13, 2008).

Official Action for U.S. Appl. No. 11/513,334 (Jan. 29, 2008).

Notification of Transmittal of the International Search Report and the Written Opinion of the International Searching Authority, or the Declaration of International Application No. PCT/US2006/033898 (Sep. 26, 2007).

Restriction Requirement for U.S. Appl. No. 11/513,334 (Sep. 13, 2007).

Troxler Electronic Laboratories "Model 6180 Troxler Tracker™ Calibration Tracking System, Manual of Operation and Instruction," PN109315, Edition 2.0 pp. 1-94 (Aug. 2007).

Sebesta et al., "New Technologies and Approaches to Controlling the Quality of Flexible Pavement Construction Performed in Cooperation with the Texas Department of Transportation and the Federal Highway Administration," Texas Transportation Institute, Report 0-4774-1 (Jun. 2006).
U.S. Department of the Army, "Engineering and Design Site Characterization and Analysis Penetrometer System (SCAPS)," EP 1110-1-32, pp. 1-14 (Nov. 1, 2005).
Kim et al., "Typical Dynamic Moduli for North Carolina Asphalt Concrete Mixtures," Final Report FWHA/NC, 2005-03 (May 2005).
Balendonck et al., "Sensors for Soil, Substrates, and Concrete Based on the MCM100 Microchip," Electromagnetic Aquametry, Springer (2005).
Chen et al., "A Correlation Between Dynamic Cone Penetrometer Values and Pavement Layer Moduli," Geotechnical Testing Journal, vol. 28, No. 1 (2005).
Daschner et al., "Determination of Composition of Foodstuffs Using MW Dielectric Spectra," Electromagnetic Aquametry, Springer, pp. 455-461 (2005).
Hauschild, "Density and Moisture Measurements Using Microwave Resonators," Electromagnetic Aquametry, Springer (2005).
Huebner et al., "Advanced Measurement Methods in Time Domain Reflectometry for Soil Moisture Determination," Electromagnetic Aquametry, Springer (2005).
Jones et al., "Thermal and Geometrical Effects on Bulk Permittivity of Porous Mixtures Containing Bound Water," Electromagnetic Aquametry, Springer (2005).
Kaatze, "Electromagnetic Wave Interactions with Water and Aqueous Solutions," Electromagnetic Aquametry, Springer (2005).
Kraszewski, "Recent Developments in Electromagnetic Aquametry," Electromagnetic Aquametry, Springer, pp. 6-11 (2005).
Kupfer, "Methods of Density-Independent Moisture Measurement," Electromagnetic Aquametry, Springer, pp. 135-165 (2005).
Kupfer, "Simulations and Experiments for Detection of Moisture Profiles with TDR in a Saline Environment," Electromagnetic Aquametry, Springer, pp. 349-365 (2005).
Sachs, "Principles of Ultra-Wideband Sensor Electronics," Electromagnetic Aquametry, Springer (2005).
Sihvola, "Model Systems for Materials with High Dielectric Losses in Aquametry," Electromagnetic Aquametry, Springer (2005).
Sovlukov, "Microwave and RF Resonator-Based Aquametry," Electromagnetic Aquametry, Springer (2005).
Stacheder et al., "Combined TDR and Low-Frequency Permittivity Measurements for Continuous Snow Wetness and Snow Density Determination," Electromagnetic Aquametry, Springer (2005).
Thakur, "Moisture Measurement in Multi-Layered Systems," Electromagnetic Aquametry, Springer (2005).
Wolter et al., "Moisture Measuring with Nuclear Magnetic Resonance (NMR)," Electromagnetic Aquametry, Springer (2005).
Zeghal et al., "Review of the New Mechanistic-Empirical Pavement Design Guide—A Material Characterization Perspective," Investing in New Materials, Products and Processes Session—2005 Annual Conference, Transportation Association of Canada, Calgary, Alberta (2005).
Hoffman et al., "Stiffness Estimates Using Portable Deflectometers," TRB Annual Meeting 2004, Washington, D.C. (2004).
Olidis et al., "Guide for the Mechanistic-Empirical Design of New and Rehabilitated Pavement Structures Materials Characterization—Is Your Agency Ready?" Applied Research Associates, Inc.—ERES Consultants Division (2004).
Sun et al., "Evaluation of a Combined Penetrometer for Simultaneous Measurement of Penetration Resistance and Soil Water Content," Journal of Plant Nutr. Soil Science, vol. 167, pp. 745-751 (2004).
Nazarian et al., "Quality Management of Flexible Pavement Layers with Seismic Methods," Center for Highway Materials Research, Research Report 1735-3F, pp. 1-40 (Dec. 2002) (Part 1 of 3).
Nazarian et al., "Quality Management of Flexible Pavement Layers with Seismic Methods," Center for Highway Materials Research, Research Report 1735-3F, pp. 41-80 (Dec. 2002) (Part 2 of 3).
Nazarian et al., "Quality Management of Flexible Pavement Layers with Seismic Methods," Center for Highway Materials Research, Research Report 1735-3F, pp. 81-120 (Dec. 2002) (Part 3 of 3).
Nelson et al., "RF Sensing of Grain and Seed Moisture Content," IEEE Sensors Journal, vol. 1, No. 2, pp. 119-126 (Aug. 2001).

Vaz et al., "Simultaneous Measurment of Soil Penetration Resistance and Water Content with a Combined Penetrometer-TDR Moisture Probe," Soil Sci. Am. Journal, vol. 65, pp. 4-12 (2001).
Nazarian et al., "Compaction Quality Control of Soils Using Wave Propagation Techniques," Center for Highway Materials Research, The University of Texas at El Paso, TRB 2001 Washington, D.C. (Nov. 2000).
Newtson et al., "Nondestructive Evaluation Using Numerical Simulation of Impact Response," ACI Materials Journal (May-Jun. 2000).
Gucunski et al., "Seismic Methods in Post Construction Condition Monitoring of Bridge Decks." Use of Geophysical Methods in Construction, Proceedings Geo-Denver (2000).
Gucunski et al., "Ann Backcalculation of Pavement Profiles from the SASW Test," Pavement Subgrade Unbound Materials and NonDestructive Testing, ED. M. Mamlouk, ASCE, Geo-Denver (2000).
Russell et al., "Design of Resilient Modulus of Subgrade Soils from FWD Tests," Pavement Subgrade Unbound Materials and NonDestructive Testing, ED. M. Mamlouk, ASCE, Geo-Denver (2000).
Nazarian et al., "Use of Instrutmented Dynamic Cone Penetrometer in Pavement Characterization," Third International Symposium on Nondestructive Testing of Pavements and Backcalculation of Moduli, ASTM Stock No. STP1375, pp. 214-228 (Jul. 1, 1999).
Chen et al., "Evaluation of In-Situ Resilient Modulus Testing Techniques," Recent Advances in the Characterization of Transportation Geo-Materials, ASCE, No. 89 (1999).
Newcomb et al., "Measuring In Situ Mechanical Properties of Pavement Subgrade Soils," Synthesis of Highway Practice 278, NCHRP, Washington DC (1999).
"C-300 Operator's Manual," Seaman Nuclear Corporation, pp. 1-80 (Copyright 1999).
Sabburg et al., "Dielectric Behavior of Moist Swelling Clay Soils at Microwave Frequencies," IEEE Transaction on Geoscience and Remote Sensing, vol. 35, No. 3, pp. 784-787 (May 1997).
Lunne et al., "Cone Penetration Testing in Geotechnical Practice," Blackie Academic and Professional Publishing (1997).
Trabelsi et al., "New Density-Independent Calibration Function for Microwave Sensing of Moisture Content in Particulate Materials," IEEE Transactions on Instrutmentation and Measurement, vol. 47, No. 3, pp. 613-622 (Jun. 1998).
Trabelsi et al., "A Microwave Method for On-Line Determination of Bulk Density and Moisture Content of Particulate Materials," IEEE Transactions on Instrumentation and Measurement, vol. 47, No. 1, pp. 127-132 (Feb. 1998).
Cutmore et al., "On-Line Measurement of Composition for the Australian Mineral and Energy Industries," IEEE Instrumentation and Measurement Technology Conference, Belgium, pp. 330-334 (Jun. 4-6, 1996).
Peplinski et al., "Dielectric Properties of Soils in the 0.3-1.3-GHz Range," IEEE Transactions on Geoscience and Remote Sensing, vol. 33, No. 3 (May 1995).
Vermeulen et al., "Continuous Measurement of Moisture in Nonconducting Materials," IEEE Transactions on Instrumentation and Measurement, vol. 41, No. 6, pp. 1023-1026 (Dec. 1992).
Scott et al., "Measured Electrical Constitutive Parameters of Soil as Functions of Frequency and Moisture Content," IEEE Transactions on Geoscience and Remote Sensing, vol. 30, No. 3, pp. 621-623 (May 1992).
Thuery, "Microwaves: Industrial Scientific and Medical Applications," Artec House, (1992).
Kraszewski, "Microwave Aquametry—Needs and Perspectives," IEE MTT, vol. 39, No. 5, pp. 828-835 (May 1991).
Arulanandan, "Dielectric Method for Prediction of Porosity of Saturated Soil," Journal of Geotechnical Engineering, vol. 117, No. 2, pp. 319-330 (Feb. 1991).
Roesset et al., "Modulus and Thickness of the Pavement Surface Layer from SASW Tests," Transportation Research Record 1260 (1990).
Badu-Tweneboah et al., "Prediction of Flexible Pavement Layer Moduli from Dynaflect and FWD Deflections," Nondestructive Testing of Pavements and Backcalculation of Moduli, ASTM STP 1026 (1989).

Chou et al., "Backcalculation of Layer Moduli from Nondestructive Pavement Deflection Data Using the Expert System Approach," Nondestructive Testing of Pavements and Backcalculation of Moduli, ASTM STP 1026 (1989).

Cosentino et al., "FWD Backcalculated Moduli Compared with Pavement Pressuremeter Moduli and Cyclic Triaxial Moduli," Nondestructive Testing of Pavements and Backcalculation of Moduli, ASTM STP 1026 (1989).

Germann et al., "Temperature, Frequency, and Load Level Correction Factors for Backcalculated Moduli Values," Nondestructive Testing of Pavements and Backcalculation of Moduli, ASTM STP 1026 (1989).

Hiltunen et al., "Influence of Source and Receiver Geometry on the Testing of Pavements by the Surface Waves Method," Nondestructive Testing of Pavements and Backcalculation of Moduli, ASTM STP 1026 (1989).

Hossain et al., "Numerical and Optimization Techniques Applied to Surface Waves for Backcalculation of Layer Moduli," Nondestructive Testing of Pavements and Backcalculation of Moduli, ASTM STP 1026 (1989).

Lytton, "Backcalculation of Pavement Layer Properties," Nondestructive Testing of Pavements and Backcalculation of Moduli, ASTM STP 1026 (1989).

Nazarian et al., "Nondestructive Evaluation of Pavements by Surface Wave Method," Nondestructive Testing of Pavements and Backcalculation of Moduli, ASTM STP 1026 (1989).

Sayyedsadr et al., "SASWOPR: A Program to Operated on Spectral Analysis of Surface Wave Data," Nondestructive Testing of Pavements and Backcalculation of Moduli, ASTM STP 1026 (1989).

Uddin et al., "In Situ Material Properties from Dynamic Deflection Equipment," Nondestructive Testing of Pavements and Backcalculation of Moduli, ASTM STP 1026 (1989).

Powell et al., "Use of a Density-Independent Function and Microwave Measurement System for Grain Moisture and Measurement," Transactions of ASAE, vol. 31, No. 6 (Nov.-Dec. 1988).

Dean et al., "Soil Moisture Measurement by an Improved Capacitance Technique, Part 1, Sensor Design and Performance," Journal of Hydrology, vol. 93, pp. 67-78 (1987).

Shimin, "A New Method for Measuring Dielectric Constant Using the Resonant Ferquency of a Patch Antenna," IEEE MTT-34, No. 9, pp. 923-931 (Sep. 1986).

Lew et al., "Relationships Between Shear Wave Velocity and Depth of Overburden," Measurement and Use of Shear Wave Velocity for Evaluating Dynamic Soil Properties, ASCE (1985).

Robertson et al., "Seismic CPT to Measure In-Situ Shear Wave Velocity," Measurement and Use of Shear Wave Velocity for Evaluating Dynamic Soil Properties, ASCE (1985).

Stokoe et al., "Use of Rayleigh Waves in Liquefaction Studies," Measurement and Use of Shear Wave Velocity for Evaluating Dynamic Soil Properties, ASCE (1985).

Stoll, "Computer-Aided Studies of Complex Soil Moduli," Measurement and Use of Shear Wave Velocity for Evaluating Dynamic Soil Properties, ASCE (1985).

Heisey et al., "Moduli of Pavement Systems from Spectral Analysis of Surface Waves", Transportation Research Record 852 (1983).

Kuraz, "Testing of a Field Dielectric Soil Moisture Meter," Geotechnical Testing Journal, vol. 4, No. 3, pp. 111-116 (Sep. 1981).

Meyer et al., "Feasibility Study of Density-Independent Moisture Measurement with Microwaves," IEEE MTT-29, pp. 732-739 (Jul. 1981).

Holtz "Introduction to Geotechnical Engineering" Prentice Hall (1981).

Topp, "Electromagnetic Determination of Soil Water Content: Measurements in Coaxial Transmission Lines," Water Resources Research, vol. 16, No. 3, pp. 574-582 (Jun. 1980).

Wobschall, "A Frequency Shift Dielectric Soil Moisture Sensor," IEEE Transactions of Geoscience Electronics, vol. GE-16, No. 2 (Apr. 1978).

Kraszewski et al., "A Preliminary Study on Microwave Monitoring of Moisture Content in Wheat," Journal of Microwave Power, vol. 12, No. 3, pp. 241-255 (Sep. 1977).

Drnevich et al., "Modulus and Damping of Soils by the Resonant Column Method," Dynamic Geotechnical Testing, ASTM STP 654, Denver, CO (Jun. 1977).

Hoar et al., "Generation and Measurement of Shear Waves In Situ," Dynamic Geotechnical Testing, ASTM STP 654, Denver, CO (Jun. 1977).

McLamore et al., "Crosshole Testing Using Explosive and Mechanical Energy Sources," Dynamic Geotechnical Testing, ASTM STP 654, pp. 30-55 (Jun. 1977).

Statton et al., "In Situ Seismic Shear-Wave Velocity Measurements and Proposed Procedures," Dynamic Geotechnical Testing, ASTM STP 654, Denver, CO (Jun. 1977).

Stephenson, "Ultrasonic Testing for Determining Dynamic Soil Moduli," Dynamic Geotechnical Testing, ASTM STP 654, Denver, CO (Jun. 1977).

Wobschall, "A Theory of the Complex Dielectric Permittivity of Soil Containing Water," IEEE Transactions on Geoscience Electron, vol. GE-15, No. 1, pp. 49-58 (1977).

Anderson, "Comparison of Field and Laboratory Shear Moduli," In Situ Measurement of Soil Properties, vol. I, North Carolina State University, Raleigh, NC, ASCE (Jun. 1-4, 1975).

Miller et al., "In Situ Impulse Test for Dynamic Shear Modulus of Soils." In Situ Measurement of Soil Properties, vol. I, North Carolina State University, Raleigh, NC, ASCE 1975 (Jun. 1-4, 1975).

Stokoe et al., "Shear Moduli of Two Compacted Fills," In Situ Measurement of Soil Properties, vol. I, North Carolina State University, Raleigh, NC, ASCE (Jun. 1-4, 1975).

Windle et al., "Electrical Resistivity Method for Determining Volume Changes that Occur During a Pressuremeter Test," In Situ Measurement of Soil Properties, vol. I, North Carolina State University, Raleigh, NC, ASCE 1975 (Jun. 1-4, 1975).

Wissa et al., "The Piezometer Probe," In Situ Measurement of Soil Properties, vol. I, North Carolina State University, Raleigh, NC, ASCE 1975 (Jun. 1-4, 1975).

Birchak et al., "High Dielectric Constant Microwave Probes for Sensing Soil Moisture," Proceedings of the IEEE, vol. 62, No. 1, pp. 93-98 (Jan. 1974).

Hipp, "Soil Electromagnetic Parameters as Functions of Frequency, Soil Density and Soil Moisture," Proceedings of the IEEE, vol. 62, No. 1, pp. 98-103 (Jan. 1974).

Hoekstra et al., "Dielectric Properties of Soils at UHF and Microwave Frequencies," Journal of Geophysical Research, vol. 79, pp. 1699-1708 (1974).

Henkel, "The Relationships Between the Effective Stresses and Water Content in Saturated Clays," Geotechnique, vol. 10 (1960).

Henkel, "The Shear Strength of Saturated Remolded Clays," Proceedings of Research Conference on Shear Strength of Cohesive Soils, ASCE, pp. 533-554 (1960).

Benson, "An Overview of Geophysical and Non-Destructive Methods for Characterization of Roads and Bridges," Use of Geophysical Methods in Construction, ASCE, 108 (2000).

Bose et al., "Dielectric Relaxation Study of Water and Water/Oil Microemulsion System," Microwave Aquametry—Electromagnetic Wave Interaction with Water-Containing Materials, IEEE (Apr. 1996).

Brandelik et al., "Measurement of Bound and Free Water in Mixtures," Microwave Aquametry—Electromagnetic Wave Interaction with Water-Containing Materials, IEEE (1996).

Gentili et al., "Analysis of Electromagnetic Sensors for Dielectric Spectroscopy by Using the (FD)2TD Method," Microwave Aquametry—Electromagnetic Wave Interaction with Water-Containing Materials, IEEE (Apr. 1996).

Gentili et al., "An Integrated Microwave Moisture Sensor," Microwave Aquametry—Electromagnetic Wave Interaction with Water-Containing Materials, IEEE (1996).

Griffin et al., "Precision of Seismic Wave Propagation Methods in Construction Applications," Use of Geophysical Methods in Construction, ASCE, 108, (2000).

Guzina, "Dynamic Soil Sensing via Horizontally-Polarized Shear Waves," Use of Geophysical Methods in Construction, ASCE, 108 (2000).

Guzina et al., "Verification and Enhancement of Portable Deflectometer Devices," http://www.mrr.dot.state.mn.us/research/MnROAD_Project/workshop2003/Base_Subgrade_Characterization_Devices.pdf (2003).

Jung, "Application of Electrical Resistivity Imaging Techniques to Civil & Environmental Problems," Use of Geophysical Methods in Construction, ASCE, 108, (2000).

Kaatze "Microwave Dielectric Properties of Water," Microwave Aquametry—Electromagnetic Wave Interaction with Water-Containing Materials, IEEE (1996).

Kendra et al., "Snow Probe for In Situ Determination of Wetness and Density," Microwave Aquametry—Electromagnetic Wave Interaction with Water-Containing Materials, IEEE (Aug. 2002).

King et al., "Material Characterization Using Microwave Open Reflection Resonator Sensors," Microwave Aquametry—Electromagnetic Wave Interaction with Water-Containing Materials, IEEE (1994).

Kobayashi, "Microwae Attenuation in a Wet Layer of Limestone," Microwave Aquametry—Electromagnetic Wave Interaction with Water-Containing Materials, IEEE (1996).

Kraszewski, "Microwave Aquametry: Introduction to the Workshop," Microwave Aquametry—Electromagnetic Wave Interaction with Water-Containing Materials, IEEE (1996).

Kraszewski et al., "Moisture Content Determination in Single Kernels and Seeds with Microwave Resonant Sensors," Microwave Aquametry—Electromagnetic Wave Interaction with Water-Containing Materials, IEEE (1996).

Kupfer, "Possibilities and Limitations of Density-Independent Moisture Measurement with Microwaves," Microwave Aquametry—Electromagnetic Wave Interaction with Water-Containing Materials, IEEE pp. 313-327 (1996).

Lin et al., "Time Domain Reflectometry for Compaction Quality Control," Use of Geophysical Methods in Construction, ASCE, 108 (2000).

Mashimo, "Free and Bound Water in Various Matrix Systems Studied by Advance Microwave Techniques," Microwave Aquametry—Electromagnetic Wave Interaction with Water-Containing Materials, IEEE, pp. 93-99 (1997).

Robinson et al., "Single- and Multiple-Frequency Phase Change Methods for Microwave Moisture Measurement," Microwave Aquametry—Electromagnetic Wave Interaction with Water-Containing Materials, IEEE (1996).

Sihvola, "Dielectric Mixture Theories in Permitivity prediction: Effects of Water on Macroscopic Parameters," Microwave Aquametry—Electromagnetic Wave Interaction with Water-Containing Materials, IEEE (1996).

Volgyi, "Integrated Microwave Moisture Sensors for Automatic Process Control," Microwave Aquametry—Electromagnetic Wave Interaction with Water-Containing Materials, IEEE, pp. 223-238 (1996).

Walker, "Accurate Percent Water Determination by Microwave Interaction Alone: 1954-Present," Microwave Aquametry—Electromagnetic Wave Interaction with Water-Containing Materials, IEEE (Apr. 1996).

Wang et al., "SH-Wave Refraction/Reflection and Site Characterization," Use of Geophysical Methods in Construction, ASCE, 108 (2000).

Xu et al., "Calculation of Sensitivity of Various Coaxial Sensors Used in Microwave Permittivity Measurements," Microwave Aquametry—Eleactromagnetic Wave Interaction with Water-Containing Materials, IEEE (Apr. 1996).

Commonly-assigned, co-pending U.S. Appl. No. 13/414,680 for "Nuclear Gauges and Methods of Configuration and Calibration of Nuclear Gauges," (Unpublished, filed Mar. 7, 2012).

Second Office Action for Chinese Patent Application No. 200980107515.9 (Oct. 18, 2012).

Non-Final Official Action for U.S. Appl. No. 12/348,784 (Jun. 20, 2012).

Second Office Action for Chinese Patent Application No. 200680040289.3 (Jun. 6, 2012).

Non-Final Official Action for U.S. Appl. No. 13/414,680 (May 30, 2012).

Final Official Action for U.S. Appl. No. 13/414,680 (Feb. 8, 2013).

* cited by examiner

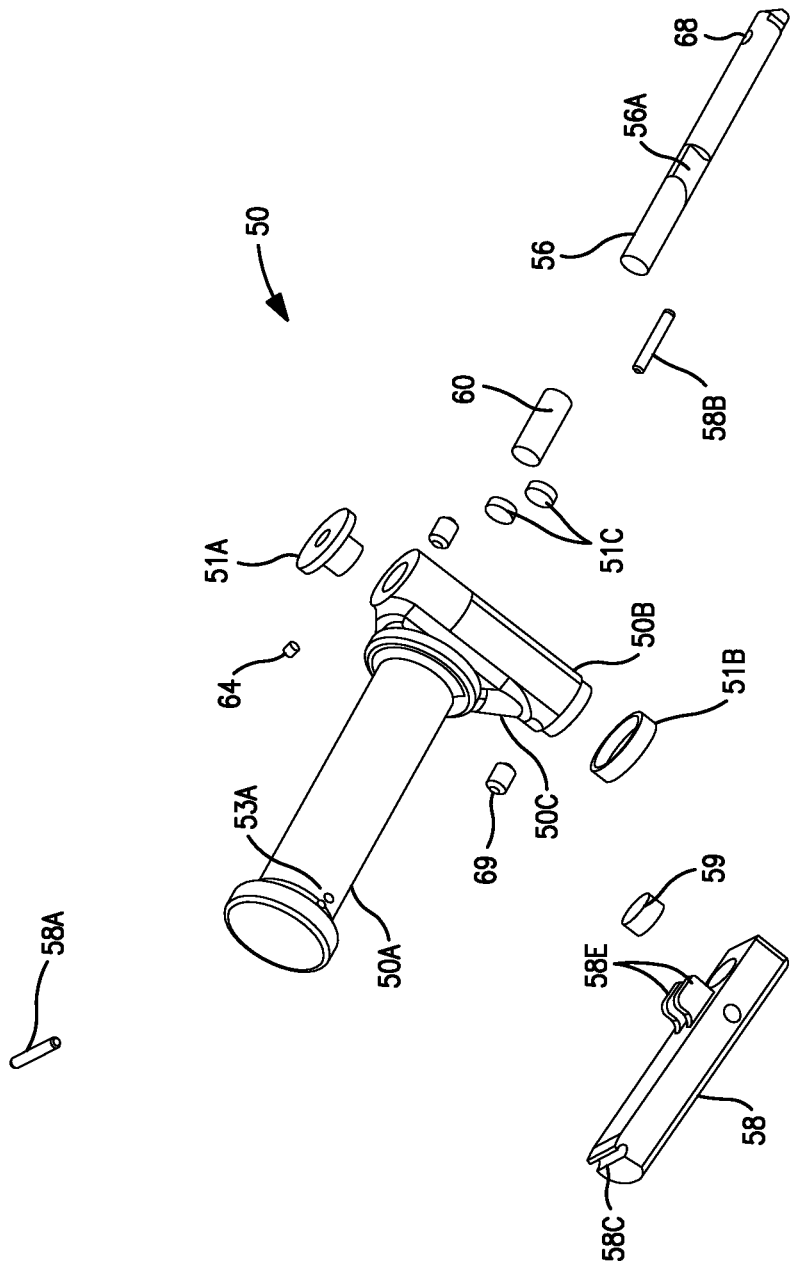
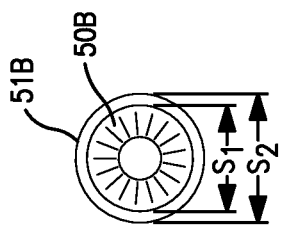
FIG. 13A
FIG. 13D

FIG. 18B     FIG. 18C

NUCLEAR GAUGES AND RELATED METHODS OF ASSEMBLY

RELATED APPLICATIONS

The presently disclosed subject matter claims the benefit of U.S. Provisional Patent Application Ser. Nos. 61/010,103, 61/010,022, and 61/010,191, all filed Jan. 4, 2008; the disclosures of which are incorporated herein by reference in their entirety.

TECHNICAL FIELD

The present subject matter generally relates to an apparatus and method for determining the density and/or moisture of materials and, more particularly, relates to nuclear gauges used in measuring the density and/or moisture of construction-related materials.

BACKGROUND

Nuclear radiation gauges have been widely used for measuring the density and moisture of soil and asphaltic materials, or other construction material. As used herein, construction material is any materials used in building roads or foundational structures including, but not limited to, soils, asphalts, asphalt-like materials, concrete, composite materials, or the like. Such gauges typically include a source of gamma radiation which directs gamma radiation into the test material, and a radiation detector located adjacent to the surface of the test material for detecting radiation scattered back to the surface. From this detector reading, a determination of the moisture and density of the material can be made.

These gauges are generally designed to operate either in a "backscatter" mode or in both a backscatter mode and direct transmission mode. In gauges capable of direct transmission mode, the radiation source is vertically moveable from a backscatter position, where it resides within the gauge housing, to a series of direct transmission positions, where it is inserted into small holes or bores in the test specimen.

Many of the gauges commonly in use for measuring density of soil, asphalt and other materials are most effective in measuring densities of materials over depths of approximately 3-12 inches. However, with the increase in cost of paving materials, the practice in maintaining and resurfacing paved roadbeds has become one of applying relatively thin layers or overlays having a thickness of one to three inches. With layers of such a thickness range, many density gauges are ineffective for measuring the density of the overlay because the density reading obtained from such gauges reflects not only the density of the thin layer, but also the density of the underlying base material.

Nuclear gauges capable of measuring the density of thin layers of materials have been developed by Troxler Electronic Laboratories, Inc. of Research Triangle Park, North Carolina. For example, thin layer density gauges are disclosed in U.S. Pat. Nos. 4,525,854, 4,701,868, 4,641,030, 6,310,936 and 6,442,232, all of which are incorporated herein by reference in their entirety. Some of the gauges disclosed in the above-referenced patents are referred to as "backscatter" gauges because the radiation source does not move outside the gauge housing, which is necessary for measurement in the direct transmission mode. In some of the gauges disclosed in the above-referenced patents, the gauge can have radiation sources that can also be extended outside of the gauge housing and into the material to be measured in a direction transmission mode. Typically, the source rods can extend up to about 12 inches.

As disclosed in the above patents, the preferred method of measuring the density of thin layers of materials, such as asphalt, is nondestructive and uses the backscatter mode. One method requires two independent density measurement systems. The geometry of these two measurement systems must be configured with respect to one another and with respect to the medium being measured in such a manner that they measure two different volumes of material. The two different volumes are not mutually exclusive insofar as they partially overlap one another. Measurement accuracy depends upon a larger portion of the volume measured by one of the measurement systems being distributed at a lower depth beneath the gauge than the volume measured by the other measurement system. This is accomplished by placing one radiation detection system in closer spatial proximity to the radiation source than the other detection system. Another volume specific measurement is typically used in soils and requires drilling a small hole in the material under test. This method is referred to as the direct transmission mode.

To prevent unneeded exposure to radiation, radiation shields have been employed to enclose the radiation source when not in use. These radiation shields encase the radiation source in a radiation shielding material such as tungsten when the source rod is in a safe position while providing a pathway for the source rod to permit exposure of the radiation source when the gauge is in use. As stated above, radiation shields are commonly made of tungsten. Lead, another radiation shielding material, is much less expensive. However, lead is soft and mechanically wears out too quickly when used as a radiation shield. Often, dirt and grit from the use of gauges finds its way into the radiation shielding where it can jam the radiation shield or cause irreparable damage to the radiation shield. There remains a need in the art for a nuclear gauge capable of operating in backscatter mode and/or direct transmission mode, and which is suitable for measuring the density and moisture of construction material.

SUMMARY

In accordance with this disclosure, nuclear gauges for determining the density and/or moisture of materials, components of such nuclear gauges, and components and methods for assembly of the same are provided. It is, therefore, an object of the present disclosure to provide nuclear gauges used in measuring the density and/or moisture of construction-related materials and methods for assembly of the gauges and their components. This and other objects as may become apparent from the present disclosure are achieved, in whole or in part, by the subject matter described herein.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which:

FIGS. 13A-13C illustrate exploded views of an embodiment of a handle used in a nuclear gauge according to the present subject matter;

FIG. 13D illustrates horizontal cross-sectional view of the handle illustrated in FIG. 13A;

FIGS. 18A-18C illustrate different views of an embodiment of a replaceable sliding guide for use in a nuclear gauge according to the present subject matter;

DETAILED DESCRIPTION

Reference will now be made in detail to the description of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

Nuclear Gauge Apparatus

Figure 1:
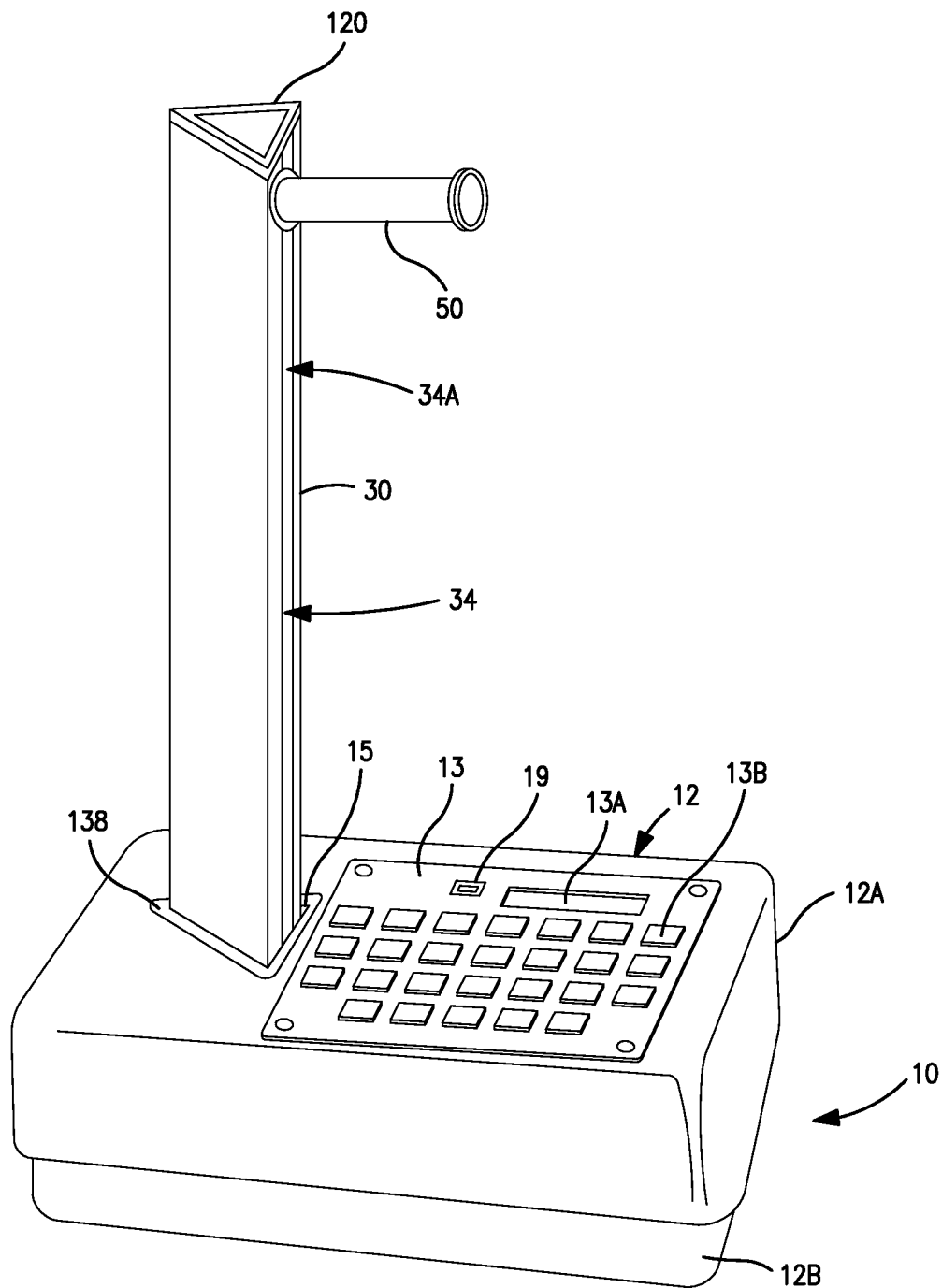
FIG. 1 illustrates a perspective view of an embodiment of a nuclear gauge according to the present subject matter.
Figure 2:
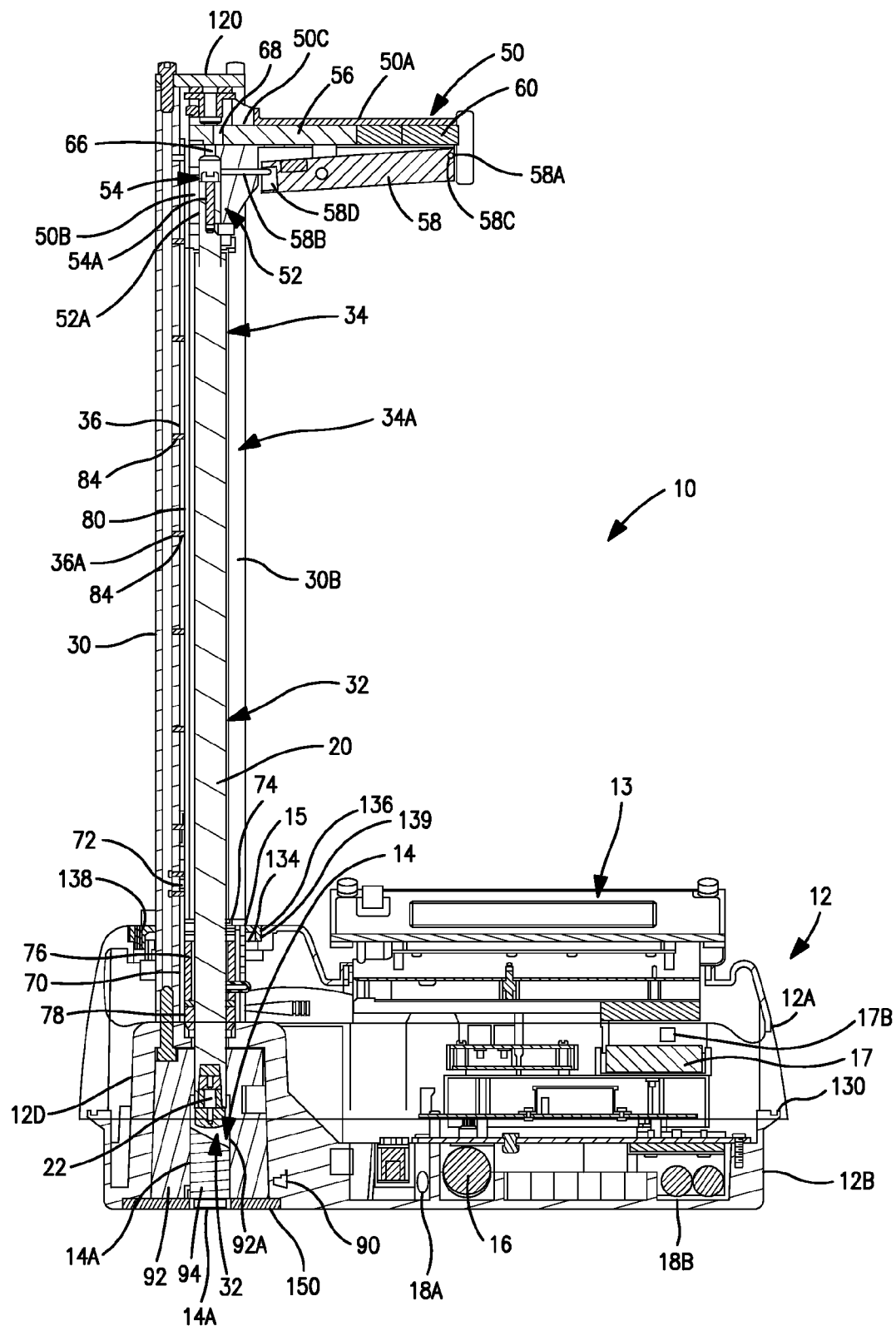
FIG. 2 illustrates a vertical cross-sectional view of the nuclear gauge illustrated in FIG. 1.
Figure 3:
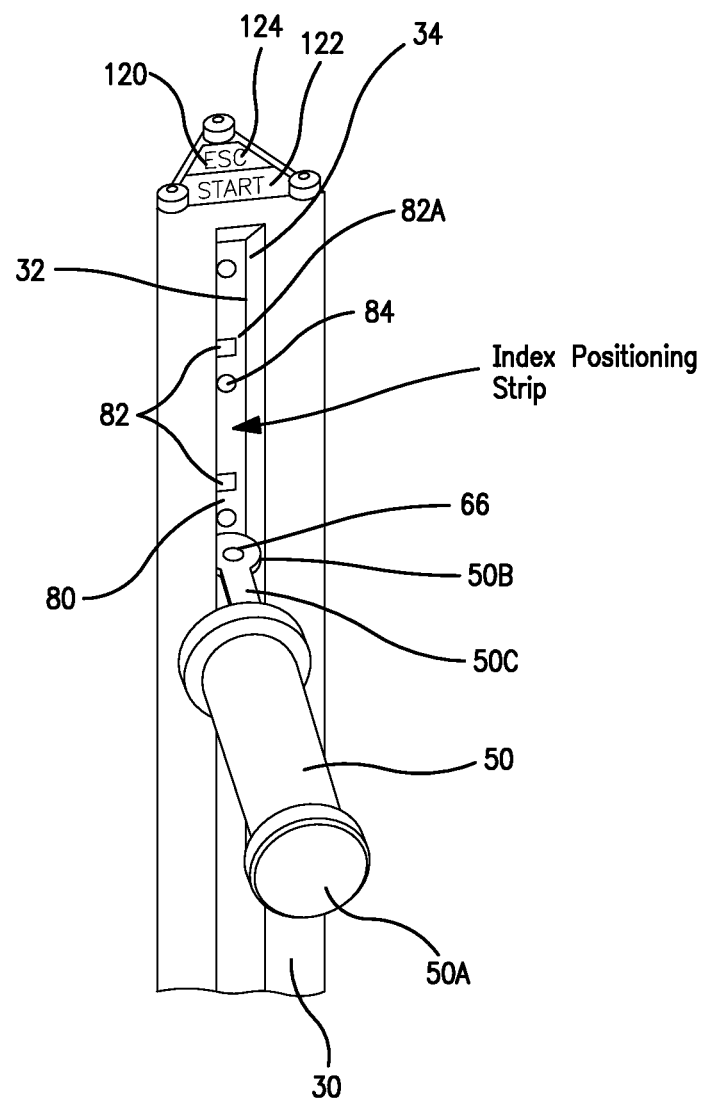
FIG. 3 illustrates a perspective view of a portion of the nuclear gauge illustrated in FIG. 1.

FIGS. 1 and 2 illustrate a nuclear gauge, generally designated 10. Different aspects and elements of gauge 10 will be briefly described with a more detailed description of the different elements provided further below. The nuclear gauge can be a density gauge, a bulk density gauge, a thin overlay gauge, a thin layer gauge, or a combination thereof.

By way of example to explain the present subject matter, the gauge 10 depicted in the figures is a thin layer gauge. However, as stated above, the gauge 10 can be other configurations of nuclear gauges. The gauge 10 can be capable of accurately measuring the density of materials, for example, thin layers of materials such as asphalt, through the use of a scattered radiation that is detected by radiation detectors. The gauge 10 can operate in both backscatter and direct transmission modes. The gauge 10 can include a gauge housing 12 and a tower 30. The gauge housing 12 and the tower 30 can form a vertical conduit 32 that extends through both gauge housing 12 and tower 30. For example, the gauge housing 12 can have a vertical cavity 14 therein and the tower 30 can include a vertical channel 34 therein that can be aligned to create the vertical conduit 32. For instance, the gauge housing 12 can include a top cover 12A and a base 12B. The base 12B can include the vertical cavity 14 therethrough. The top can include an opening 15 through which the tower 30 can pass. The tower 30 can be disposed on the base 12B of the gauge housing 12 so that the vertical channel 32 aligns with the vertical cavity 14 to form a vertical conduit 34 through the tower 30 and the gauge housing 12.

The gauge 10 can include a user interface 13 that is located on the top cover 12A of the gauge housing 12. The user interface 13 can be in communication with a central processing unit (CPU) 17 that controls the gauge 10 and runs the associated tests. For example, the user interface 13 can include a screen 13A and keypad 13B that can be used to input the parameters of the tests to be run on the nuclear gauge 10.

Figure 14:
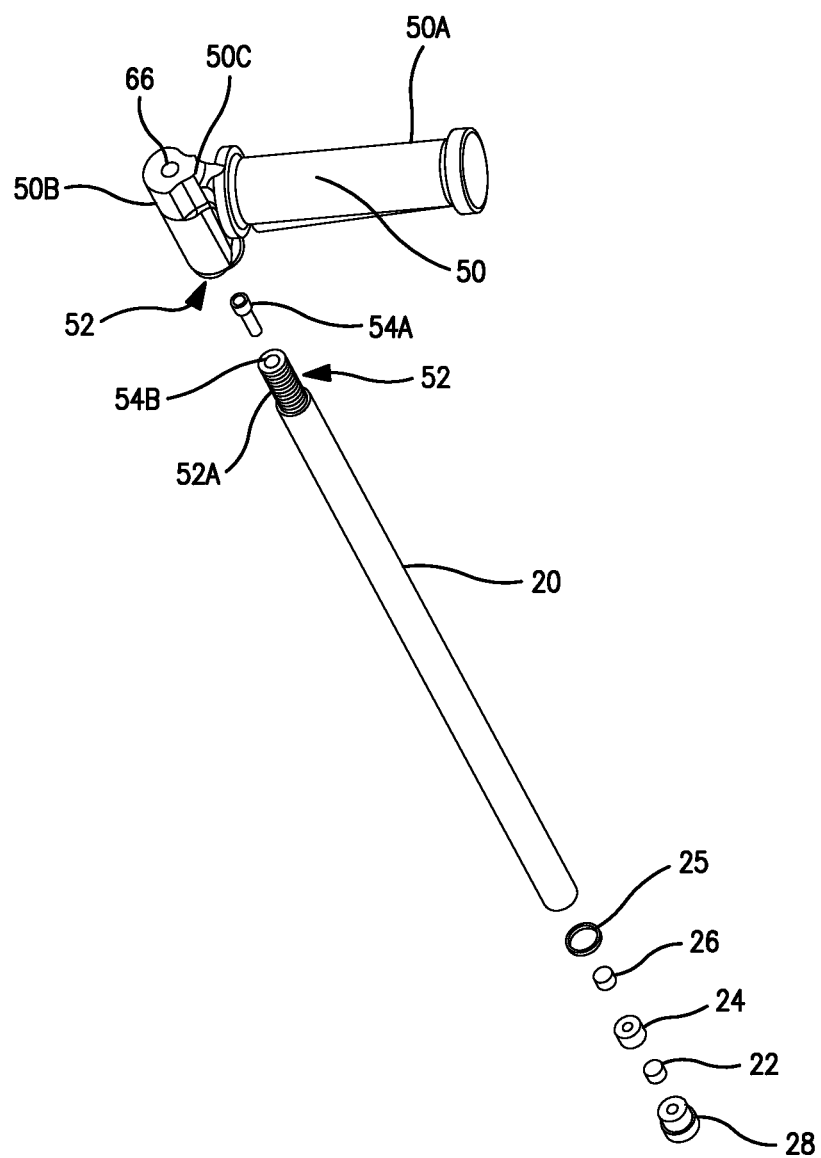
FIG. 14 illustrates an exploded view of an embodiment of a source rod and handle according to the present subject matter.
Figure 15:
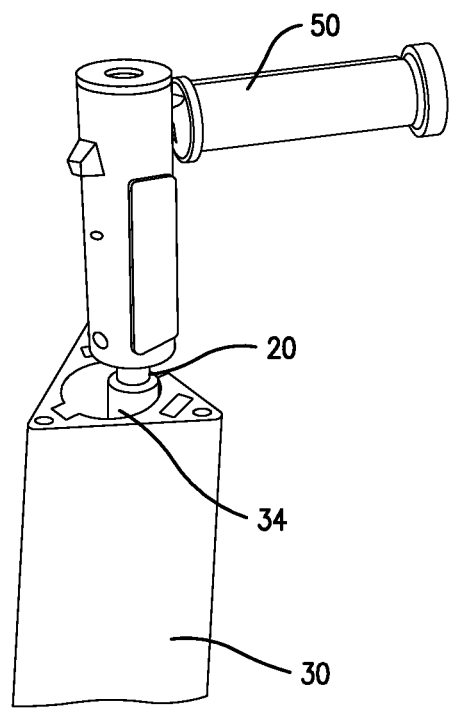
FIG. 15 illustrates a perspective view of an embodiment of a source rod being inserted a support tower, or source rod housing, according to the present subject matter.

The gauge 10 can include a vertically moveable source rod 20 containing a radiation source 22 in a distal end thereof. As shown in FIG. 14, the source rod 20 can include a spacer 24, a ring weld 25, a source spring 26 and a source plug 28. The radiation source 22 may be any suitable radiation source, such as $^{137}$Cs radiation source or $^{60}$Co. The source rod 20 can reside in the vertical conduit 32 created by the vertical channel 34 of the tower 30 and the vertical cavity 14 in the gauge housing 12.

The gauge 10 can include at least one density measurement system that utilizes at least one radiation detector. For example, as shown in FIG. 2, the gauge 10 can include two separate density measurement systems. The geometry of these two measurement systems is configured with respect to one another and with respect to the medium being measured in such a manner that they measure two different volumes of material. The two different volumes are not mutually exclusive insofar as they partially overlap one another. Measurement accuracy depends upon a larger portion of the volume measured by one of the measurement systems being distributed at a lower depth beneath the gauge than the volume measured by the other measurement system. This is accomplished by placing one radiation detection system in closer spatial proximity to the radiation source than the other detection system. To accomplish this, the gauge 10 includes a first radiation detector 18A and a second pair of radiation detectors 18B, wherein the first radiation detector 18A is located in closer spatial proximity to the radiation source 22. The radiation detectors, 18A and 18B, for example, may be any type of gamma ray radiation detector. For instance, the radiation detectors, 18A and 18B, can include preferably Geiger Mueller tubes, but can also include scintillation detectors, or proportional counters. The radiation detectors, 18A and 18B, can be located adjacent to the base 12B of the gauge housing 12. The gauge 10 can also include a moisture detector 16 that can use to measure the moisture of such construction material.

The gauge 10 can also include a handle 50 that is secured to the source rod 20 for vertically extending and retracting the source rod 20. The handle 50 along with a guide and sealing system 70 facilitate the guidance of the source rod 20 through the vertical conduit 32 created by the vertical channel 34 in the tower 30 and the vertical cavity 14 in the base 12B of the gauge housing 12. The handle 50 can be used to move the source rod to a plurality of predetermined source rod locations so as to change the spatial relationship between the radiation source and the at least one radiation detector. The handle 50 includes a coarse adjustment mechanism 52 and a fine adjustment element 54 for adjusting the height of the source rod 20 for positioning the radiation source 22 relative to the radiation detectors 18A, 18B to provide proper measurement at the different predetermined source rod locations. In particular, the source location at backscatter is extremely important and should be very precise.

To provide the predetermined source rod locations, an indexing mechanism can be provided. For example, as shown in FIGS. 2-6, an index positioning strip 80 can be placed in the tower 30 that can be engaged by the handle 50 to hold the source rod 20 at a predetermined source rod location. The index positioning strip 80 can include index holes 82 therein. The index holes 82 can serve as notches that the handle 50 engages as will be explained in more detail below. The index holes 82 can be uniformly spaced apart from each other. For example, the index holes 82 can be spaced apart at interval distances of about one inch, about two inches or about three inches.

The tower 30 can include an indexing groove 36 that is adjacent and opens into the vertical channel 34. The index positioning strip 80 can be secured in the indexing groove 36. The index positioning strip 80 can have apertures 84 for accepting fasteners 84, such as screws, rivets or the like that engage the tower 30. The index positioning strip 80 having index holes 82 therein can be securable at a designated location within the vertical channel 34 of the tower 30 to create the notches. Further, the index positioning strip 80 can be adjustable within the tower 30.

A depth strip 100, as shown in FIGS. 9-12, can be positioned in the tower 30 and can provide a non-contact measurement of the source position. The depth strip can use optical sensors, such as optical range finder sensors, acoustic sensors, magnetic sensors and the like to provide non-contact measuring of the positioning of the source rod. The depth strip 100 can include a parting line 100A with the depth strip 100 being convertible from a 12-inch unit to an 8-inch unit along the parting line 100A. Another parting line can be included on the depth strip to create a depth strip that can be used in a backscatter only gauge. To house the depth strip 100, the tower 30 can include a measurement compartment 38. Depending on the type of depth strip 100, the measurement compartment 38 can be a separate channel or passageway for housing the depth strip.

The gauge 10 also includes a radiation shield assembly 90 as shown in FIGS. 2 and 17-24. The radiation shield assembly 90 includes a safety shield 92 that is coaxially mounted in the base 12B of the gauge housing. The safety shield 92 helps to define the vertical cavity 14 in the base 12B of the gauge housing 12. For example, the base 12B is formed to create a shield housing 12D through which an opening passes. The safety shield 92 has a passage 92A passing therethrough. The safety shield 92 fits into the shield housing 12D so that the opening in the shield housing 12D aligns with the passage 92A in the safety shield 92. The aligned opening in the shield housing 12D and the passage 92A through the safety shield 92 can create the vertical cavity 14.

Instead of just using a cover plate 150 to hold the safety shield 92 in place in the gauge housing, one or more set screws 93 can secure the safety shield 92 in place by screwing the one or more set screws 93 into one or more corresponding screw holes 93A in the shield housing 12D. The use of the set screws 93 to hold the safety shield 92 in place in the shield housing 12D simplifies assembly and increases productivity during manufacturing. The assembler does not have to hold the safety shield 92 in place while trying to insert the rest of the components of the radiation shield assembly 90. Further, the use of set screws 93 permits the safety shield to be pre-molded and inspected for quality control prior to assembly, thereby eliminating the need to pour molten lead into the base 12B of the gauge housing 12 at the time of assembly.

Figure 21:
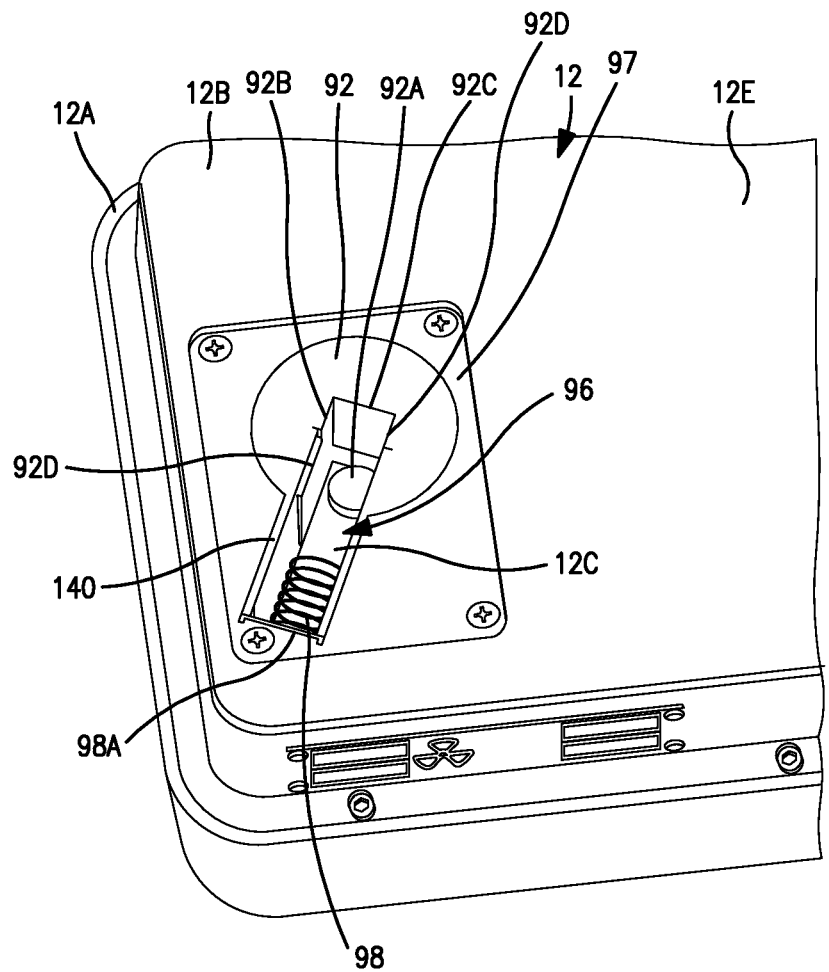

The radiation shield assembly 90 also includes a sliding block 94 that is positionable to move laterally between two positions relative to the safety shield 92. The sliding block 94 can reside in a first position blocking a distal end of the vertical cavity 14 such that radiation is shielded from exiting the cavity. The sliding block 94 can also reside in a second position adjacent to the vertical cavity. In the second position, the source rod 20 can move vertically through the radiation shield assembly 90 and the base 12B of the gauge housing 12. The base 12B of the gauge housing 12 and the safety shield 92 can define a track 96 configured to receive the sliding block 94 and guide movement of the sliding block 94. For example, a shield track segment 92B can be defined in the safety shield 92 that comprises at least a portion of the track 96. The shield track segment 92B and the passage 92A can intersect and merge at the lower end of the safety shield 92 as shown in FIG. 21.

Figure 22:
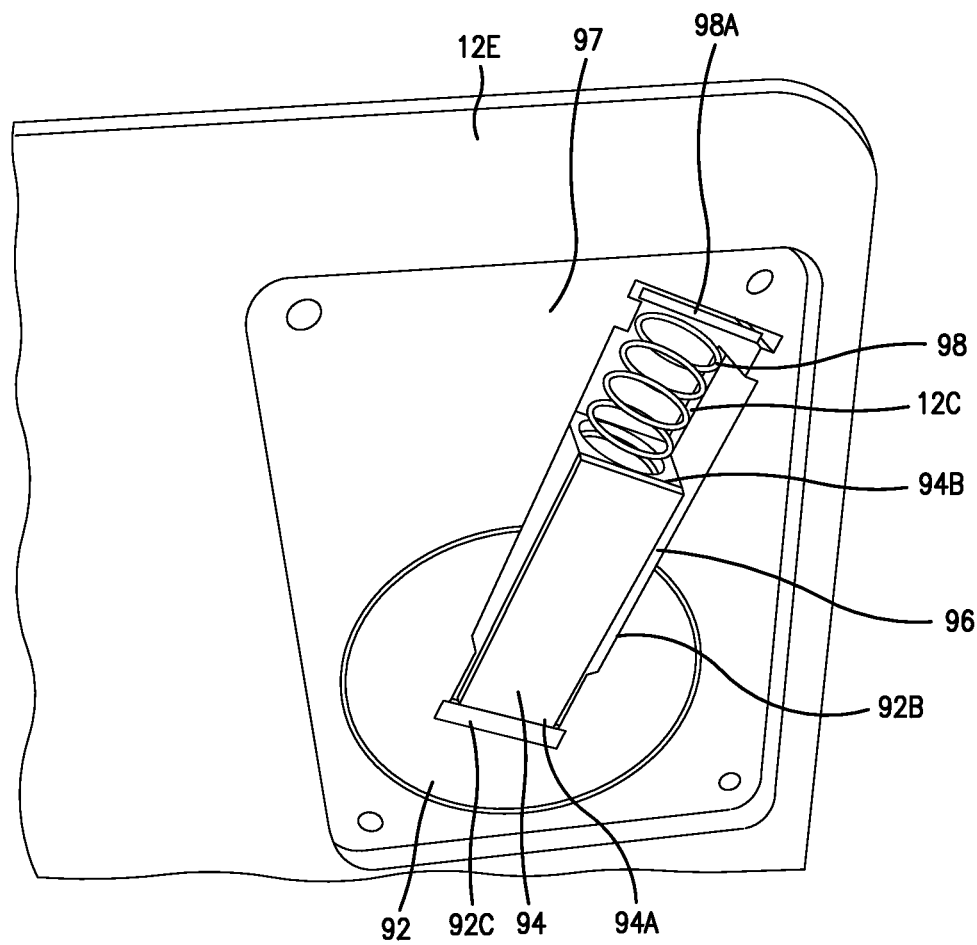

The base 12B of the gauge housing 12 can include a base track segment 12C. The base track segment 12C and the shield track segment 92B can be aligned to form the track 96. The sliding block 94 can be placed in the track 96 formed by the base track segment 12C and the shield track segment 92B. In the first position of the sliding block 94, the sliding block 94 extends through the shield track segment 92B such that an end 94A of the sliding block abuts against an interior wall 92C of the safety shield 92 as shown in FIG. 22. The portion of the interior wall 92C that the sliding block 94 abuts can comprise a hardened material, such as hardened steel, as will be explained in more detail below. In this first position, the vertical cavity 14 and the vertical conduit 32 which it partially forms are closed by the sliding block 94. In the second position of the sliding block 94, the end 94A of the sliding block 94 is moved away from the interior wall 92C of the safety shield 92 so that the vertical cavity 14 and the vertical conduit 32 which it partially forms are opened so that the source rod 20 can emerge. In such a position, the sliding block 94 is adjacent the vertical cavity 14.

A spring 98 can engage the sliding block 94 to bias the sliding block 94 into the first position. The spring 98 can engage the end 94B of the sliding block 94. Further, base 12 can include a spring guide 98A. The spring 98 can reside between the spring guide 98A and the end 94B of the sliding block 94.

As shown in FIG. 2, the safety shield 90 and sliding block 94 of the radiation shield assembly 90 are operatively positioned to minimize the user's exposure to radiation when the radiation source 22 is in the safe position. The safety shield 90 can be constructed of lead or tungsten. However, other radiation shielding material may be used. The sliding block 94 can also comprise radiation shielding material such as tungsten.

In addition to avoiding wear in some locations, it can be desirable to allow the sliding of two components. For example, the sliding block 94 closes the vertical conduit 32 in which the source rod 20 resides and that passes through the safety shield 92 when the source rod 20 moves back to safe position. By adding material in the correct location, the friction between these two components can be kept low and dirt resistance kept high. One or more replaceable sliding guides 140 can help accomplish this. The replaceable sliding guides 140 can be placed on either side of the sliding block 94 at least partially between the sliding block 94 and the side walls of the safety shield 92 that can form the track 96 as will be explained in more detail below.

The gauge 10 can include a remote user interface that can be used to initiate a measurement of the gauge 10 in addition to the user interface 13 on the gauge housing 12. For example, the remote user interface can be a remote keypad 120 as shown in FIGS. 1-3 and 25B. The remote keypad 120 can be located on a top of the tower 30 and distal from the gauge housing 12. The remote keypad 120 can comprise multiple switch states. The states can include a start switch 122 and an escape switch 124. The start switch 122 can be used to begin a gauge count or other tests once the gauge 10 and source rod 20 are in a proper position. The escape switch 124 can be used to abort such tests. The tower 30 can include a routing compartment 39 for routing the electrical wiring for the second keypad 120 into the gauge housing 12 for connection with the CPU 17. The routing compartment 39 can be a separate channel or a passageway within the tower 30. Alternatively, the remote keypad can be a wireless control mechanism, such as a fob, which is physically separated from the gauge 10 and is in wireless communication with the gauge 10.

An embodiment of the tower 30, handle 50, radiation shield assembly 90 and other related features will now be described in more detail. The tower 30 as shown in FIGS. 1-8 provides sturdiness and durability to protect the source rod 20. The tower 30 can substantially surround the source rod 20. The tower 30 provides a structure that supports the source rod 20 and limits the amount of stress placed on the source rod 20 that can occur by an unintended clockwise or counterclockwise torque. Such torque can occur when the source rod 20 is in a safe position. Thereby, the tower 30 provides a stiffer source rod 20 positioning as compared to gauges without a tower. The tower 30 can have any cross-sectional shape. For example, the tower 30 may have a cross-section that is circular, square, rectangular or the like. Further, as shown in the Figures, the tower 30 can have a triangular cross-section. The tower 30 can comprise a metal or a hardened plastic. For example, the tower 30 can be extruded aluminum.

Figure 4A:
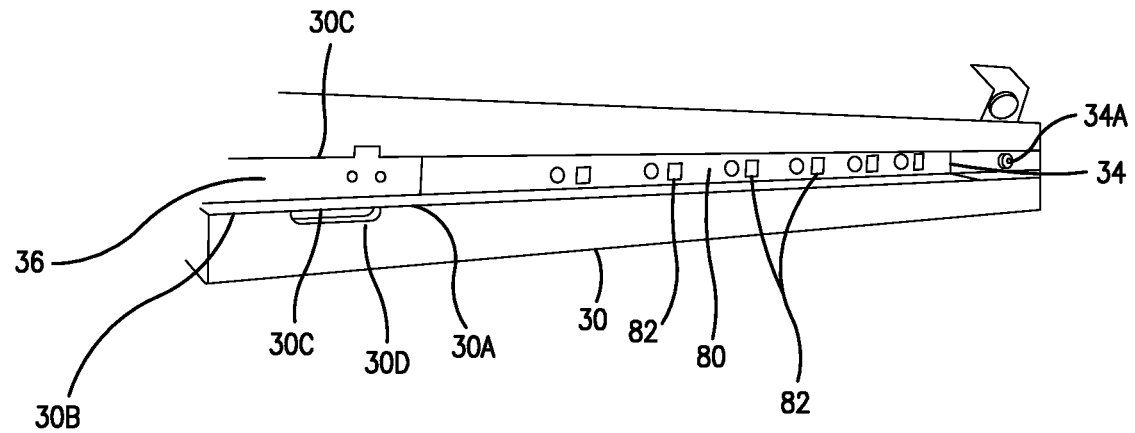
FIG. 4A illustrates a perspective view of an embodiment of a support tower, or source rod housing, used in a nuclear gauge according to the present subject matter.
Figure 4B:
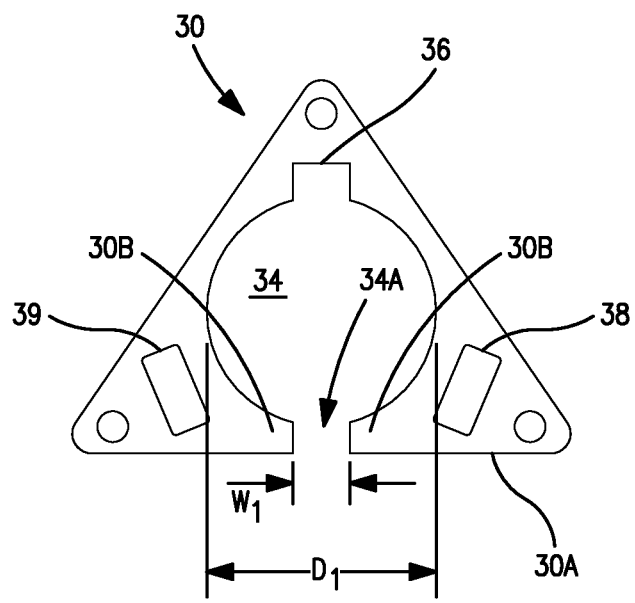
FIG. 4B illustrates a horizontal cross-sectional view of the support tower illustrated in FIG. 4A.

The channel 34 in tower 30 is wide enough to provide sufficient clearance for the source rod. For example, as shown in FIG. 4B, the channel 34 can have a circular cross-sectional diameter $D_1$ that provides easy movement of the source rod 20 therein. The channel 34 can have an inlet 34A that is formed by edges 30B and opens to a side 30A of the tower 30. The handle 50 affixed to the source rod 20 can be configured to slidably engage the inlet 34A. Handle 50 can have a grip portion 50A that extends outward from the tower 30, an engagement portion 50B that is adjustably connected the source rod 20 and a neck portion 50C that is disposed between the grip portion 50A and the engagement portion 50B. The inlet 34A can have a width $W_1$ in which the neck portion 50C can reside. The width $W_1$ of inlet 34A can be less than the diameter or width of the source rod 20.

Figure 13B:
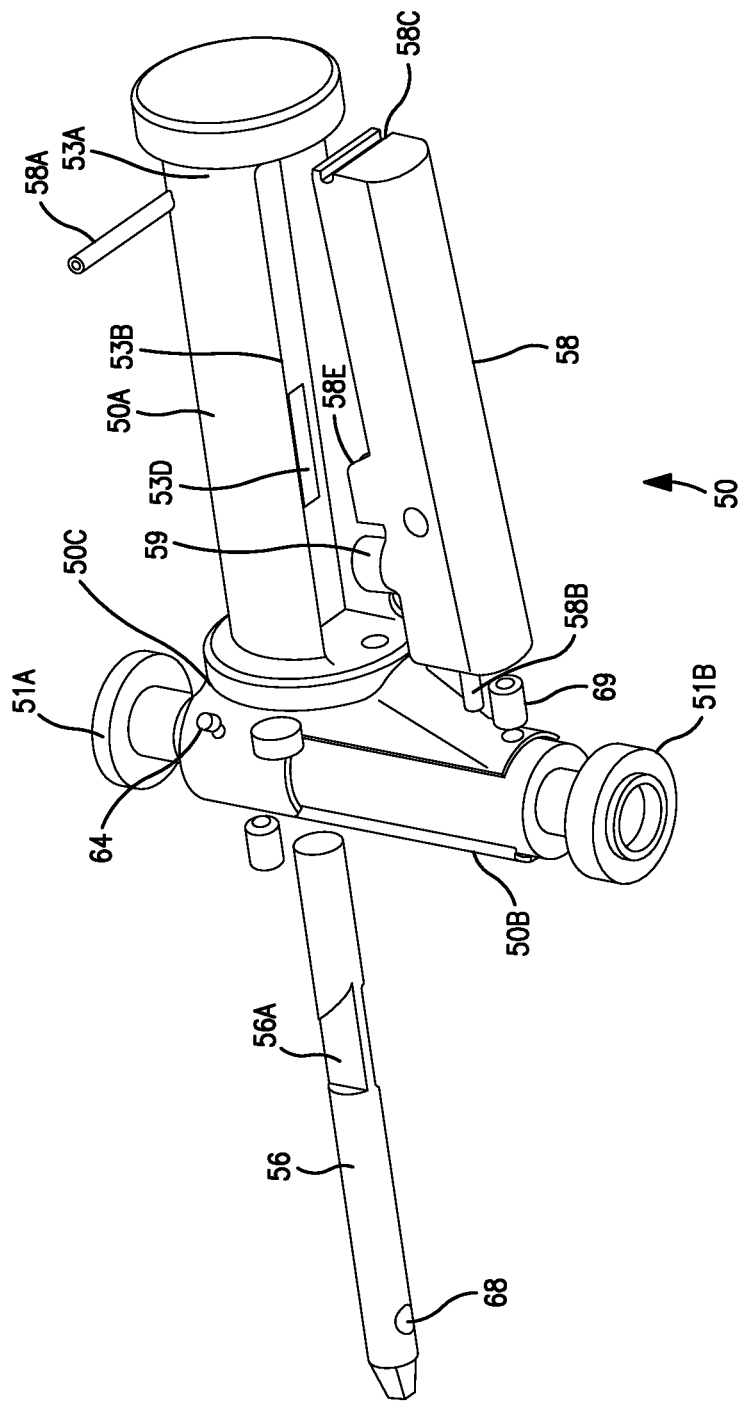
Figure 13C:
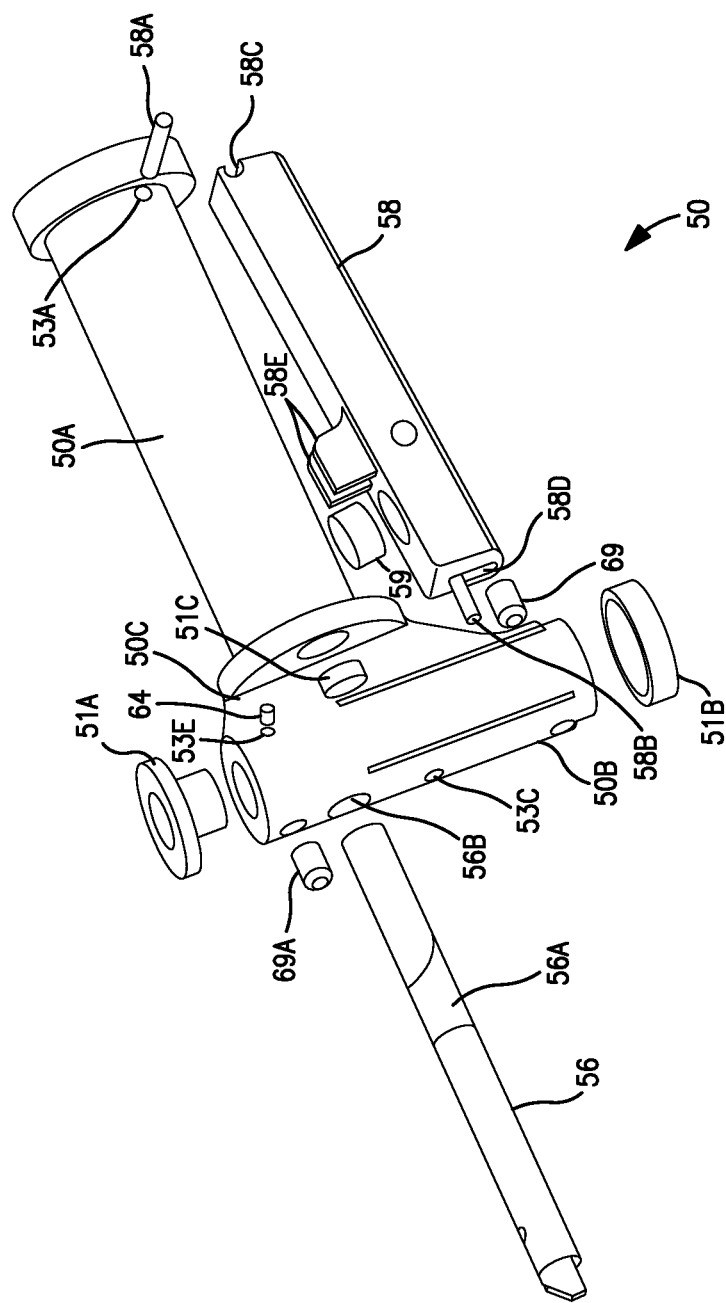

The engagement portion 50B can be configured to slidably engage the channel 34. For example, the handle 50 can include slider pads 51C and/or at least one slider disc as shown in FIG. 13C. In the embodiment shown in FIGS. 13A-13D, a top slider disc 51A and a bottom slider disc 51B are provided that are positioned on either end of the engagement portion 50B of the handle 50. The slider discs 51A, 51B can have a cross-sectional shape taken in a plane parallel to the grip portion 50A of the slider discs 51A, 51B that is larger than the cross-sectional shape of the engagement portion 50B. For example, the cross-sectional view of the engagement portion 50B below the grip portion 50A and the neck portion 50C illustrated in FIG. 13D shows the outer diameter $S_2$ of the of the bottom slider disc 51A being larger than the outer diameter $S_1$ of the engagement portion 50B. The cross-sectional shapes of the top and bottom slider discs 51A, 51B can be approximately the same size. For example, the outer diameters of the top and bottom slider discs 51A, 51B can be equal. The outer diameters of the top and bottom slider discs 51A, 51B can be similar in size to the diameter $D_1$ of the vertical channel 34 of the tower 30. Thereby, the slider discs 51A, 51B can enhance the stability of the source rod 20 in the vertical channel 34 of the tower 30 and can assist in reducing radial movement of the source rod 20 at the end engaged by the handle 50.

The slider discs 51A, 51B can be at least partially formed from a friction reducing material. For instance, the slider discs 51A, 51B can have an outer perimeter that interfaces with the tower 30 in the vertical channel 34 that is a friction reducing material. For example, the slider discs 51A, 5B can be or can include a polymer having a low coefficient of friction. The polymer can be at least one of polytetrafluoroethylene, perfluoroalkoxy, and fluorinated ethylene propylene.

The handle 50 can include a plunger 56 and a trigger 58. The plunger 56 can be extendable to engage index holes 82 of the index positioning strip 80 disposed within the tower 30 and retractable to disengage the index holes 82 by actuation of the trigger 58. The trigger 58 can be located on the underside of the grip portion 50A of the handle 50. The trigger 58 can be held in place by a pair of pins 58A, 58B. The end of the trigger 58 distal from the neck portion 50C of the handle 50 can have a pivot groove 58C that engages pivot pin 58A to create a pivot point for the trigger 58. The pivot pin 58A can reside in the pivot aperture 53A defined in the grip portion 50A. The trigger 58 can include a vertical extending slot 58D as shown in FIGS. 2 and 13C that can engage locking pin 58B. The slot 58D permits the trigger 58 to be moved up and down with the pin 58B residing in the slot 58D. A trigger spring 59 can engage the trigger 58 at a position on the trigger closer to the slot 58D and more distal from the groove 58C. The trigger spring 59 biases the trigger 58 away from the plunger 56. The handle 50 can also include a spring 60 that engages the plunger 56 and a spring guide 62 within the grip portion 50A. The spring 60 biases the plunger 56 towards an extended position.

The trigger 58 can include at least one protrusion 58E that engages at least one retraction groove 56A on the plunger 56. In the embodiment shown, two protrusions 58E are provided on the trigger 58 and two retraction grooves 56A are provided on the plunger 56. However, it is understood that one or more protrusions and corresponding retraction grooves may be provided.

The protrusions 58E can be slanted to match a slant in the groove 56A. The slant of the protrusions 58E and the retraction grooves 56A are such that, as the trigger 58 is squeezed upward, the protrusions 58E engage the retraction grooves 56A forcing the plunger 56 to a retracted position. Once the source rod is moved to one of the predetermined source rod locations that is aligned with a corresponding index hole 82, the trigger 58 can be released. The trigger spring 59 biases the trigger 58 away from the plunger 56 and the spring 60 biases the plunger 56 towards an extended position with the plunger 56 engaging the corresponding index hole 82.

Figure 5:
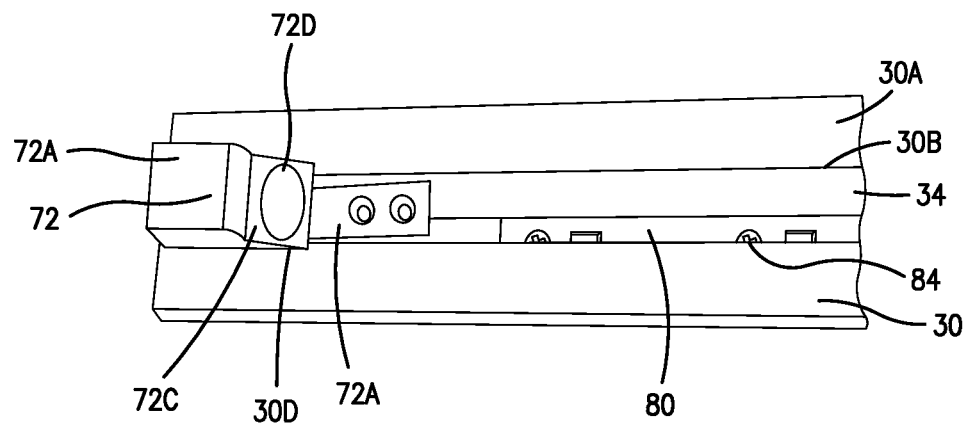
FIG. 5 illustrates a close-up perspective view of the support tower illustrated in FIG. 4A.
Figure 6:
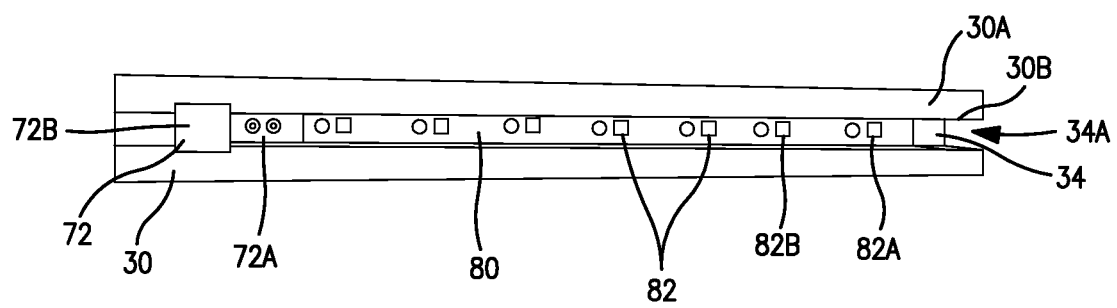
FIG. 6 illustrates a perspective view of the support tower illustrated in FIG. 4A.
Figure 7A:
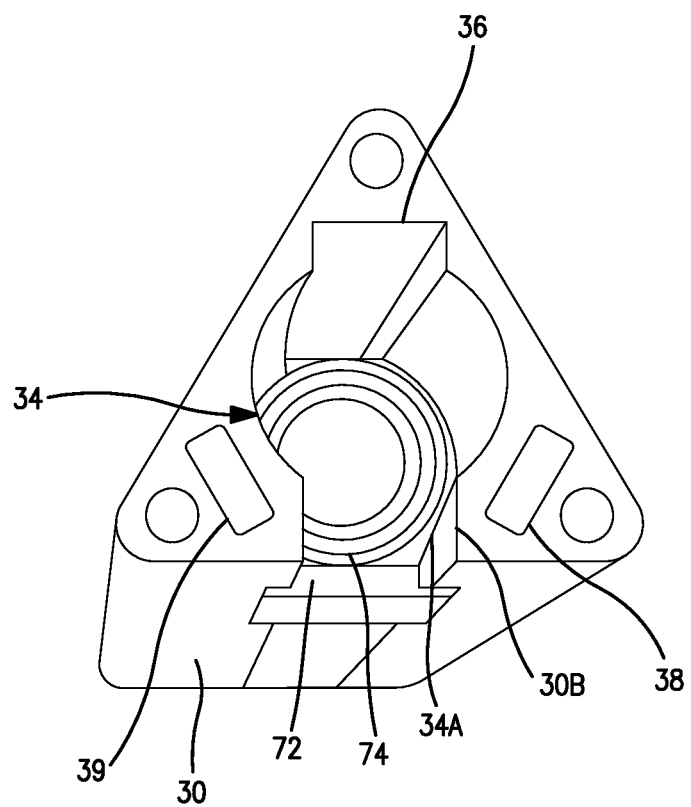
FIG. 7A illustrates a perspective end view of the support tower illustrated in FIG. 4A.
Figure 7B:
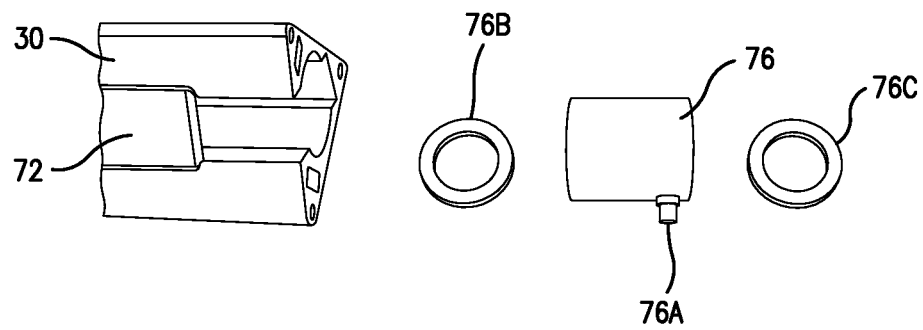
FIG. 7B illustrates a perspective view of the support tower illustrated in FIG. 4A and an embodiment of a tube spacer to be inserted into the tower according to the present subject matter.
Figure 7C:
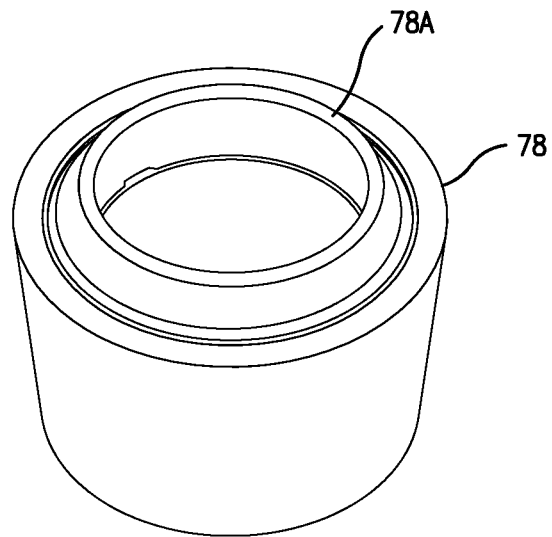
FIG. 7C illustrates a perspective view of an embodiment of a source rod bearing to be inserted into a support tower, or source rod housing, according to the present subject matter.
Figure 8:
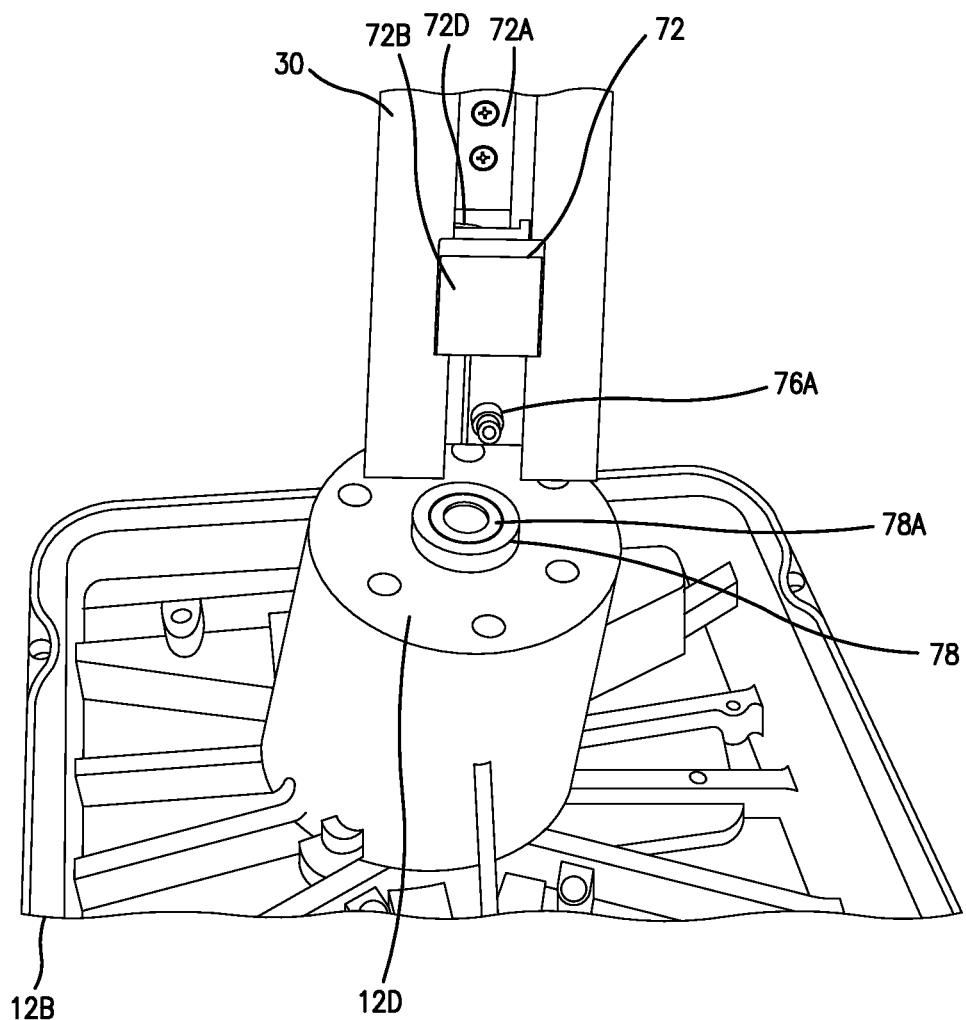
FIG. 8 illustrates a perspective view of an embodiment of a support tower, or source rod housing, and base of a gauge housing according to the present subject matter.

The index holes 82 of the index positioning strip 80 can provide different source rod locations by holding the source rod 20 at different positions as shown in FIGS. 2-6. These locations can include, for example, index hole 82A as shown in FIG. 6 that corresponds to the "safe" position wherein the radiation source 22 is raised and shielded from the test material. The safe position is used to determine the standard count. Another index hole 82B corresponds to the backscatter mode wherein the radiation source 22 is located adjacent to the surface of the test material underlying the gauge 10. Other index holes 82 can correspond to a plurality of direct transmission positions. The use of the index positioning strip 80 with its adjustability permits less stringent manufacturing tolerances. Therefore, the index positioning strips 80 allow greater variability with this design. Thus, the position of the strip 80 can be adjusted for additional manufacturing flexibility. The strip 80 can be attached in different manners. For example, the tower 30 can include adjustment screw holes 36A (see FIG. 2) that can align with apertures 84 in strip 80 for insertion of screws. Thus, adjustment screw holes 36A and apertures 84 can be used to secure the strip 80 to the tower 30. The index positioning strip 80 can be convertible to a length that can be used with a 12-inch source rod, an 8-inch, or to a length that is usable with a backscatter only gauge.

The safe position corresponding to the index holes 82A can position the tip of the source rod 20 at least about 2.20 inches above the outer surface of the base 12B of the gauge housing 12. This places the radiation source 22 in a position that exhibits reduced sensitivity of the standard count to slight radiation source positioning variability in the vertical direction. Specifically, the radiation standard count rate with the radiation source 22 in the safe position changes only about 2-10 scaled counts per mil of radiation source position change in the vertical direction in the gauge 10.

Figure 9:
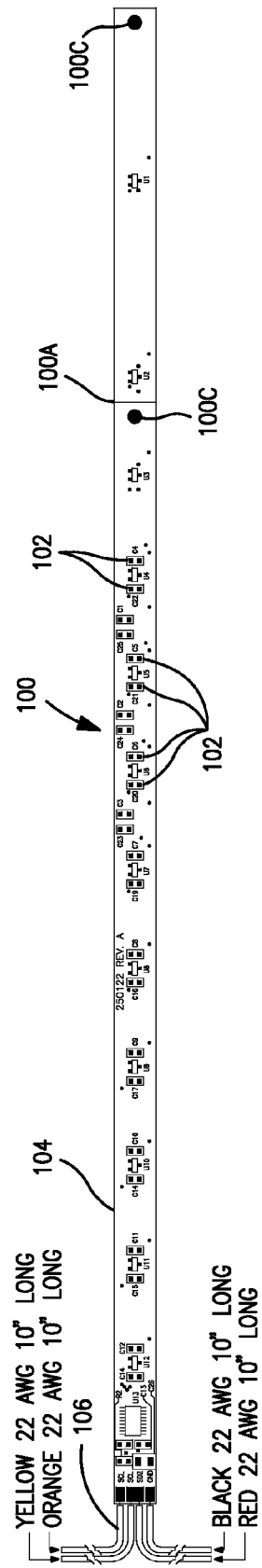
FIG. 9 illustrates a plan view of an embodiment of a depth strip that can provide a non-contact measurement in a nuclear gauge according to the present subject matter.
Figure 10:
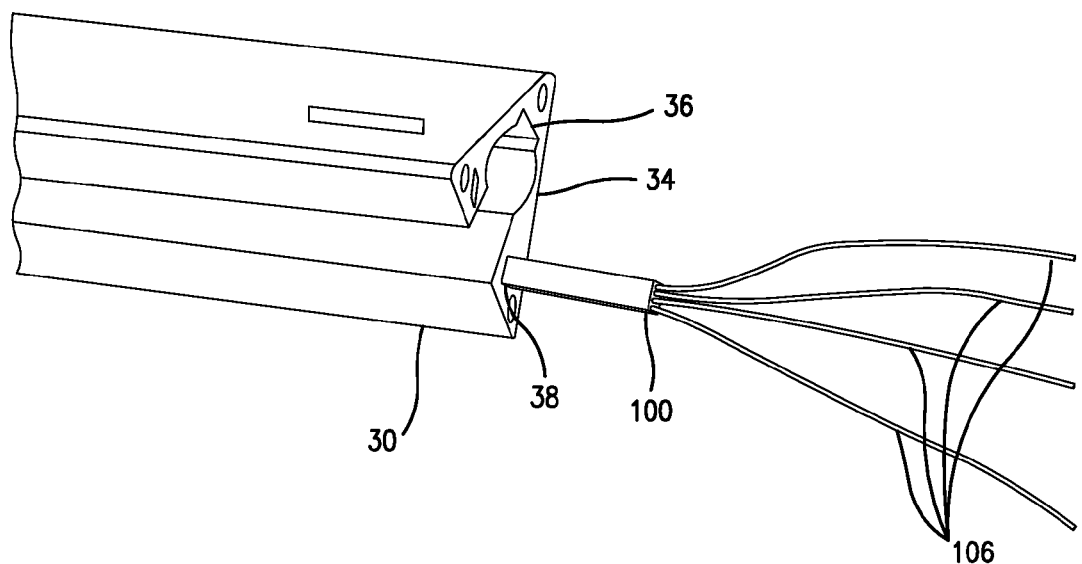
FIG. 10 illustrates a perspective view of an embodiment of a support tower, or source rod housing, and depth strip according to the present subject matter.
Figure 11:
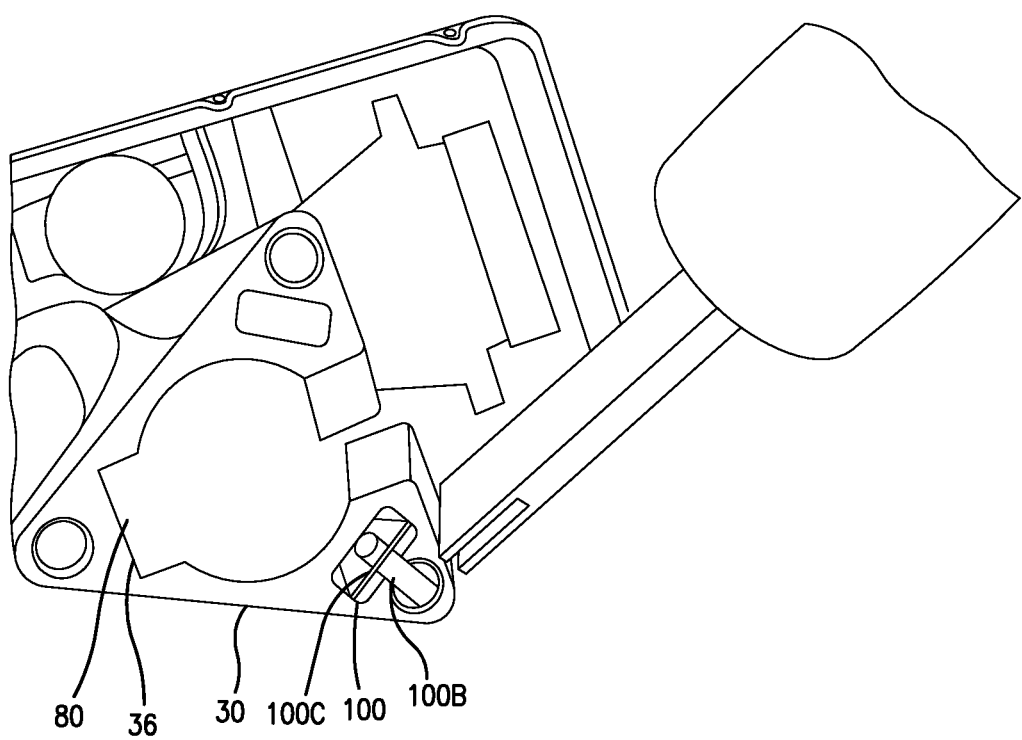
FIG. 11 illustrates a perspective end view of the support tower and depth strip illustrated in FIG. 10.
Figure 12:
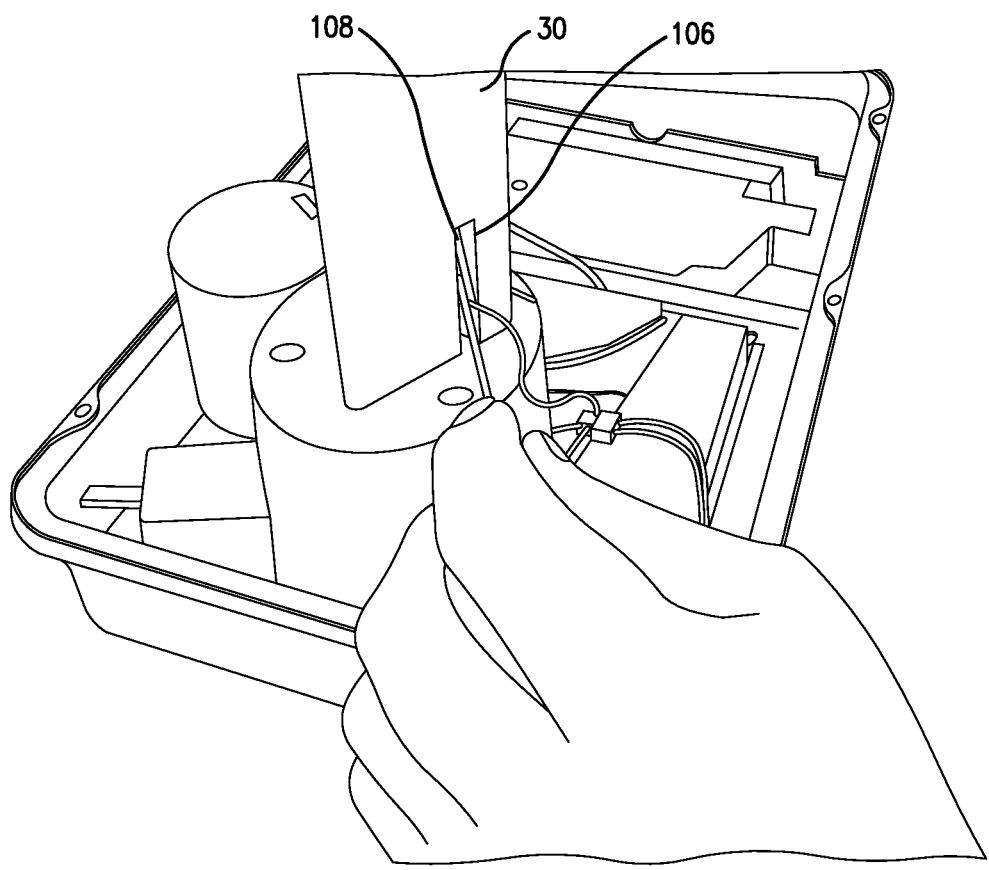
FIG. 12 illustrates a perspective view of an embodiment of a support tower and base of a gauge housing according to the present subject matter.

As illustrated in FIGS. 9-11, a depth strip 100 can be positioned in the tower 50 and can provide non-contact measurements used to determine the depth at which the source rod 20 is positioned during use. For example, the tower 50 can include a measurement compartment 38 in which the depth strip 100 can be placed. The measurement compartment 38 can be a channel or groove. Alternatively, the compartment 38 can be a passageway within the tower 30 in proximity to the vertical channel 34 in which the source rod 20 resides. As stated above, the depth strip can use optical sensors, such as optical range finder sensors, acoustic sensors, magnetic sensors and the like to provide non-contact measuring of the positioning of the source rod.

As described above, the depth strip 100 that resides in the measurement compartment 38 can be a sensor that uses magnetically actuated, low power Hall Effect sensors 102 as the means to determine the rod position. For example, the Hall Effect sensors 102 of the depth strip 100 can be alignable with the index holes 82 of the index positioning strip 80. The Hall Effect sensors 102 can be mounted on a printed circuit board 104 at discrete positions which are spaced about one inch and/or about two inches apart. The printed circuit board 104 can include other electronics to power the Hall Effect sensors 102, determine which Hall Effect sensor 102 is activated, and communicate this information with the gauge CPU 17 that is in communication with the user interface 13. This configuration allows for absolute location of the source rod, not just relative to the safe position.

The handle 50 can include a magnet 64 thereon that is detectable by the Hall Effect sensors 102 to provide non-contact measuring of the positioning of the source rod 20. The Hall Effect sensors 102 can be placed on the printed circuit board 104 so that they will line up with the magnet 64 located on the handle 50 of the moveable source rod 20. The source rod 20 can be then "indexed", such that it can only be placed in discrete positions through the use of the index positioning strip 80. These positions can be about one inch or about two inches apart. Special indexing is also achievable by replacing the strip. At each of these discrete positions, the magnet 64 in the handle 50 can be positioned directly across from one of the Hall Effect sensors 102 on the printed circuit board 104. Thus, only one of the Hall Effect sensors 102 is actuated at a time. When the user starts a gauge operation that is source rod position sensitive, the CPU 17 can communicate with the printed circuit board 104 electronics to determine which Hall Effect sensor 102 is activated. The CPU 17 software can be structured such that it can relate the actuated Hall Effect sensor 102 to a known index position. If a Hall Effect sensor 102 is not actuated, the CPU 17 can inform the gauge user that the source rod 20 is not in a valid position. If a Hall Effect sensor 102 is actuated, the CPU 17 can start the gauge operation, and pass the index position to the software. In this manner, the gauge user does not have to manually enter the source rod position.

By including a parting line 100A along the printed circuit board 104, the depth strip 100 is convertible from a 12-inch unit to an 8-inch unit along the parting line. In this manner, a single designed depth strip 100 can be used in different gauges 10 that have two different distances at which the source rod 20 can extend.

To facilitate proper movement of the source rod 20 within the vertical conduit 32 formed by the vertical channel 34 in the tower 30 and the vertical cavity 14 in the gauge housing 12, the guide and sealing system 70 can be provided. The guide and sealing system 70, as shown in FIGS. 1, 2 and 4-8, can work in conjunction with the at least one slider disc on the handle 50, such as slider discs 51A, 51B, to increase stability and minimize radial movement of the source rod 20. The guide and sealing system 70 can include a bracket 72 that can be placed and secured in the vertical channel 34 of the tower.

The bracket 72 can have a first end portion 72A that is configured to lie flat within the groove 36 in the tower 30. The first end 72A portion can be secured below the index positioning strip 80, but aligned with the index positioning strip 80 within the groove 36. The bracket 72 can also have a second end portion 72B that is configured to reside outside of the channel 34 of the tower 30. For example, as shown in FIGS. 4-6, the second end portion 72B can be wider than the width $W_1$ of the inlet 34. The tower 30 can have a groove 30C cut into each of the edges 30B on either side of the inlet 34A of the channel 34. The second end portion 72B can be configured to reside in the grooves 30C. The second end portion 72B can extend substantially parallel to the first end portion 72A of the bracket 72. Between the first end portion 72A and the second end portion 72B, the bracket 72 can include a mid-portion 72C. The mid-portion 72C can be substantially perpendicular to both the first end portion 72A and the second end portion 72B and also about perpendicular to the vertical channel 34 in which the source rod is disposable. The mid-portion 72C includes a bracket aperture 72D through which the source rod can pass. The edges 30B can also include slots 30D through which the bracket 72 including the mid-portion 72 can pass so that when the bracket 72 is secured in the tower 30, the first end portion 72A resides within the groove 36, the second end portion 72B resides within the grooves 30C, and the mid-portion 72B extends through the slots 30D and into the vertical channel 34 so that the bracket aperture 72D aligns with the vertical channel 34 to accept the passage of the source rod 20 therethrough.

The guide and sealing system 70 (see FIG. 2) can also include an upper seal 74 that can be placed into the vertical channel 34 below the bracket 72 so that the upper seal abuts against the underside of the mid-portion 72C of the bracket. The upper seal 74 can have an inner diameter that is less than the diameter of the bracket aperture 72D and is in close tolerance of the source rod 20. The outer diameter of the upper seal 74 can be substantially similar to the diameter $D_1$ of the vertical channel 34. After the upper seal 74 is seated against the bracket 72, a tube spacer 76 with a grease fitting 76A can be seated against the upper seal 74. The guide and sealing system 70 can also include a source bearing 78 that can be secured against the tube spacer 76 at the end distal from the bracket 72 and upper seal 74. The source rod bearing 78 can include a seal wiper 78A that acts as a lower seal. The source rod bearing 78 can be seated in the shield housing 12D of the base 12B above the radiation shield assembly 90. The tube spacer 76 can include a top washer 76B and a bottom washer 76C that can be placed on either end of the tube spacer. For example, top washer 76B can be placed on the end of the tube spacer 76 proximate to the upper seal 74 and the bottom washer 76C can be placed at the end of the tube spacer 76 proximate to the source rod bearing 78.

The source rod bearing 78 can be a bushing. The source rod bearing 78 can guide the source rod 20 through cavity 14 in the gauge housing 12 with an extremely close fit to the source rod 20 in order to minimize variability in radiation source positioning. Specifically, the outer diameter of source rod bearing 78 can be about 1.1265 inches +/−about 0.0005 of an inch and the bearing inner diameter can be about 0.6265 of an inch +/−about 0.0005 of an inch. Additionally, the bearing housing diameter can be about 1.1265 inches +/−0.0005 of an inch. The source rod 20 diameter can be about 0.625 of an inch +/−about 0.001 of an inch. This results in a nominal bearing clearance of about 0.00025 of an inch and a bearing clearance range of press-fit to about 0.001 of an inch. The nominal source rod clearance can be about 0.00175 of an inch and the source rod clearance range can be from about 0.0005 to about 0.0030 of an inch. Thus, the source rod 20 has a total range of radial movement of no more than about 0.0005 of an inch to about 0.0040 of an inch. Since the desired position of the source rod 20 is on the true centerline of the source rod bearing 78, the movement away from true center is actually the radial clearance, which equals one-half of the diametrical clearance. Thus, the maximum movement away from true center of the source rod 20 can be about one-half of 0.0040 of an inch, or 0.0020 of an inch.

It is important to correctly calibrate the height of the source rod 20 to ensure that the source rod 20 will be at the correct depths when the handle engages the index positioning strip 80. To calibrate the gauge 10, the exact source height can be adjusted in real time by the assembly technician using only a screwdriver or a wrench. To calibrate the gauge 10, the exact source height can be adjusted in real time by the assembly technician using only a wrench or a screwdriver. The screwdriver or wrench can be inserted in or onto a threaded device, such as a screw or bolt 54A that is securely affixed to the source rod 20 such that the screw does not rotate separately from the source rod 20. Any type of finely pitched thread device can be used. A screw such as a flathead screw, slotted screw, a Phillips head screw, a star screw such as those sold under the name TORX®, a spline drive screw, hex screw, double hex screw or the like, can be used as the fine adjustment element 54. Similarly, an Allen Head screw can be used.

Access can be permitted to the screwdriver or wrench through the top of the tower 30 and the handle 50. The remote keypad 120 or other top portion is removed. The handle 50 can define at least one adjustment aperture therein to permit access to the fine adjustment element 54. For example, the handle 50 includes adjustment apertures 66 and 68 as shown in FIGS. 2, 13B, and 14 in both the engagement portion 50B and the plunger 56, respectively, so that when the source rod 20 is in backscatter position all the adjustment apertures 66 and 68 in the handle 50 are aligned within reach of the assembly technician's screwdriver or wrench. In the embodiments where the handle 50 can include a plunger 56 and a trigger 58, the plunger 56 can define an adjustment aperture 68 that aligns with the adjustment aperture 66 in the handle 50 when the plunger 56 resides in an extended position.

The coarse adjustment mechanism 52 and fine adjustment element 54, as shown in FIGS. 2 and 14, can be used to set the height of the source rod 20 during manufacturing with the settings being semi-permanent. "Semi-permanent" as used herein means that the height of the source rod 20 cannot be reset without physical manipulation through the use of chemical and/or mechanical tools. The handle 50 can also include one or more set screws 69 for holding and locking the source rod 20 in place after the height of the source rod 20 is adjusted with the coarse adjustment mechanism 52 and the fine adjustment element 54. The source rod 20 can be in a backscatter position when the height of the source rod 20 is adjusted with the coarse adjustment mechanism 52 and the fine adjustment element 54. This ability greatly reduces assembly time, improves locating precision and repeatability.

Within the handle 50, the coarse adjustment mechanism 52 can include a threaded section 52A and the fine adjustment element 54 can include a screw, such as an Allen Head screw 54A. Such an Allen Head screw 54A can be securely affixed to the source rod 20 such that the screw does not rotate separately from the source rod 20.

The coarse adjustment mechanism 52 permits the quick attachment of the source rod 20 into the handle 50. The fine adjustment element 54 uses the threaded section 52A as well, but fine adjustment element 54 permits for very small incremental movement of the source rod 20 through partial rotation of the source rod 20. The fine adjustment element 54 can permit accurate and acute adjustment of the height of the source rod of less than about one hundredth of an inch. For example, the fine adjustment element 54 can permit adjustment of the source rod 20 to plus or minus about 0.005 of an inch. In some embodiments, the fine adjustment element 54 can permit adjustment of the source rod 20 to plus or minus about 0.001 of an inch. Thus, both coarse adjustments and fine adjustments can be made to the source rod height.

Figure 16:
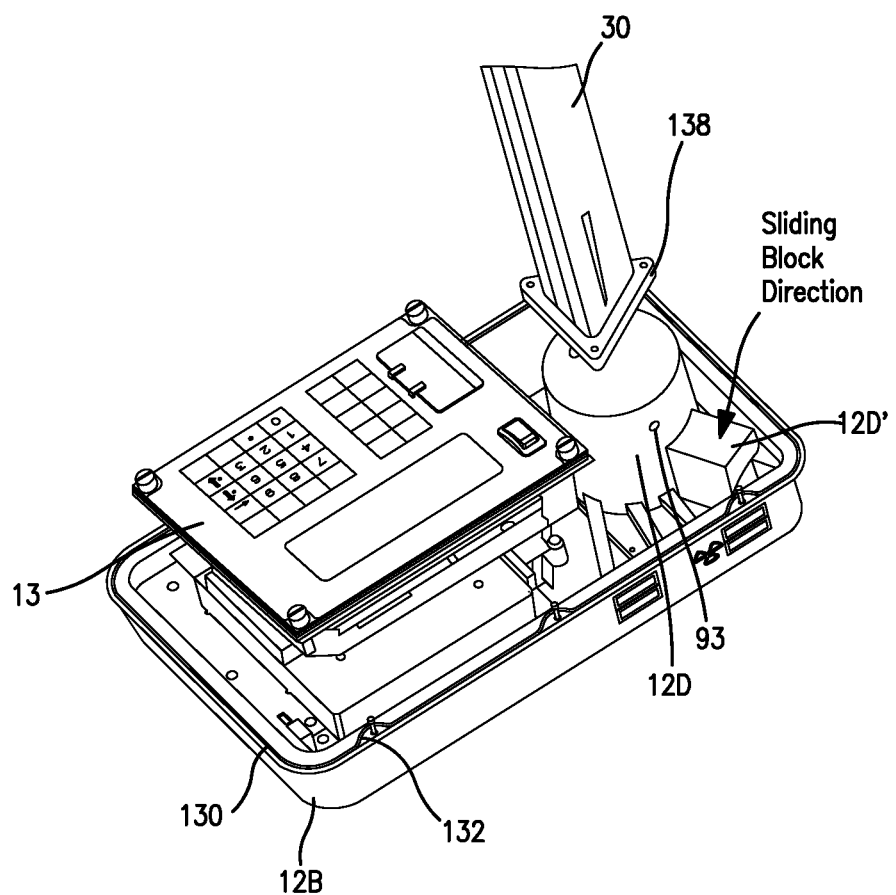
FIG. 16 illustrates a perspective view of an embodiment of a nuclear gauge according to the present subject matter.

In the past, attempts have been made to keep water out of the gauges. Humidity and water can adversely affect the high voltage electronics. The problem has always been to develop a seal that allows the source to move freely up and down while completely blocking humidity and moisture. To protect the electronics contained within the gauge housing 12 of the gauge 10, precautions can be taken to ensure a good seal is created between the top cover 12A and the base 12B of the gauge housing 12 and between the tower 30 and the gauge housing 12. For example, as shown in FIG. 16, an O-ring 130 can be positionable in a groove 132 within the base 12B of the gauge housing 12 between the base 12B and the top cover 12A. The O-ring 130 can extend around an outer parameter of the base 12B with the top cover 12A engaging the O-ring 130 to create water proof seal between the top cover 12A and the base 12B.

Further, as shown in FIGS. 2 and 25A-25C, a second O-ring 134 having a diameter which fits tightly around the cross-section of the tower 30 can be positioned at the tower base where the tower 30 is secured to the gauge housing 12. The use of the O-ring 134 and a trim plate 138 that fit around the horizontal cross-sectional shape of the tower 30 and engage the top cover 12A of the gauge housing 12 allows the entire circumference of the sealing area to be water tight. This can be especially important in gauges that are specified for all weather use. For example, the cross-section of the tower 30 can be triangular in shape and the top cover 12A can form a groove 136 around opening 15 into which tower 30 can extend. A triangular trim plate 138 having an outer lip 139 can push the second O-ring 134 against the tower 30 to create a water resistant seal. The trim plate 138 can be placed around the tower base and over this second O-ring 134 and then secured to the gauge housing 12.

The radiation shield assembly 90 is described below in more detail. As stated above, the radiation shield assembly 90 has a portion that is operatively positionable to move laterally between two positions. A first position is provided for blocking a distal end 14A of the vertical cavity 14 of the gauge housing 12 such that radiation is shielded from exiting the cavity 14. A second position adjacent to the vertical cavity 14 is provided for allowing vertical movement of the source rod 20 through the radiation shield assembly 90. As described above, the radiation shield assembly 90 can include a sliding block 94 positionable to move laterally between the first position and the second position. A track 96 can be configured to receive the sliding block 94 and guide movement of the sliding block 94. A spring 98 can engage the sliding block 94 and bias the sliding block 94 into the first position.

A safety shield 92 can be included in the radiation shield assembly 90. The safety shield 92 can include a shield track segment 92B therein that comprises at least a portion of the track 96. The base 12B of the gauge housing 12 can include a base track segment 12C. The base track segment 12C and the shield track segment 92B are alignable to form the track 96.

At least one replaceable sliding guide 140, as shown in FIGS. 17 and 18A-18C, is positionable within the track 96 adjacent the sliding block 94. The at least one replaceable sliding guide 140 is configured to reduce friction as the sliding block 94 moves between the first position and the second position. The at least one replaceable sliding guide 140 can comprise two replaceable sliding guides 140 with each replaceable sliding guide 140 extending over at least a portion of the base track segment 12C and the shield track segment 92B on opposing walls of the track 96.

Figure 17:
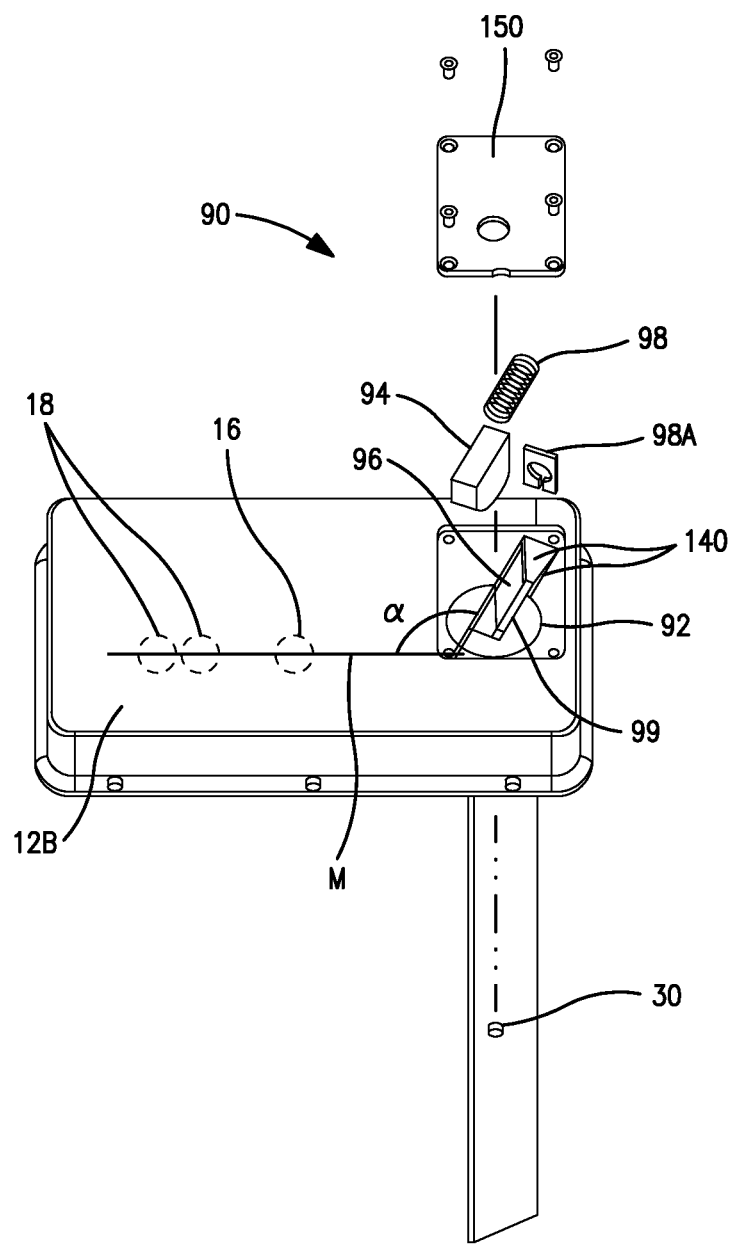
FIG. 17 illustrates a partially exploded bottom view of an embodiment of a nuclear gauge according to the present subject matter.

The track 96 is configured to extend in a direction within the nuclear gauge 10 so that, as the sliding block 94 moves from the first position to the second position, the sliding block 94 moves away from the radiation detector(s) 18A, 18B as shown in FIG. 16 with the sliding block housing 12D'. The track 96 can extend at an angle α of between about 90° and about 180° as measured from a plane M extending between the radiation detector(s) 18A, 18B and the point of the track 96 closest to the radiation detector 18A as shown in FIG. 17. In some embodiments, the track 96 can extend at an angle α of between about 100° and about 135°. The angle α of the track can bias the sliding block 94 toward a closed position due to gravity when the gauge is placed in a carrying case and the carrying case is in its upright position. Further, at such an angle, the effect of the sliding block 94 on the reading of the gauge 10 is minimized as any leakage of radiation is directed away from the detectors.

As stated above, the safety shield can be a molded block. The safety shield 92 can be made of lead. Alternatively, the safety shield 92 can be tungsten or a tungsten and lead mix. For example, the safety shield 92 can comprise concentric cylinders of lead and tungsten. The shield track segment 92B can include two opposing side walls 92D extending into the safety shield 92 and an end wall 92C disposed between the side walls 92D (see FIG. 21) within the safety shield 92 with at least a portion of the end wall 92C within the safety shield 92 comprising a hard surface material. The safety shield 92 can include wear plates, or inserts, of a hard surface material that forms the end wall 92C. The hard surface material can comprise at least one of steel, hardened steel, high carbon steel, stainless steel, tungsten or the like.

Figure 18A:
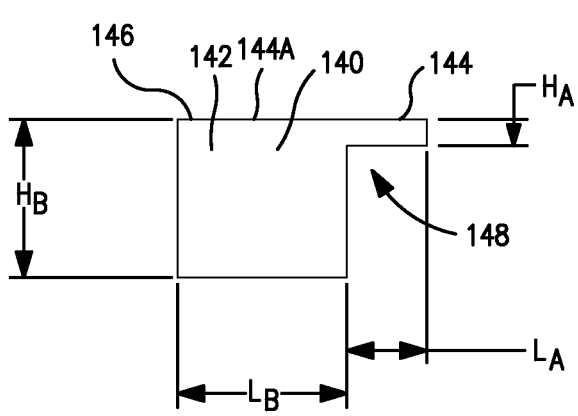
Figure 18A:
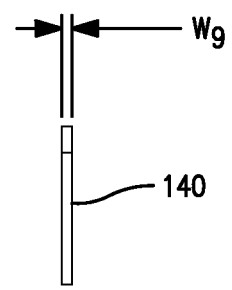
Figure 18A:
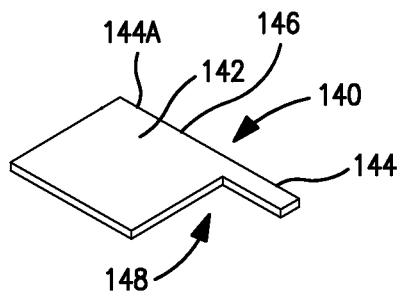
Figure 19:
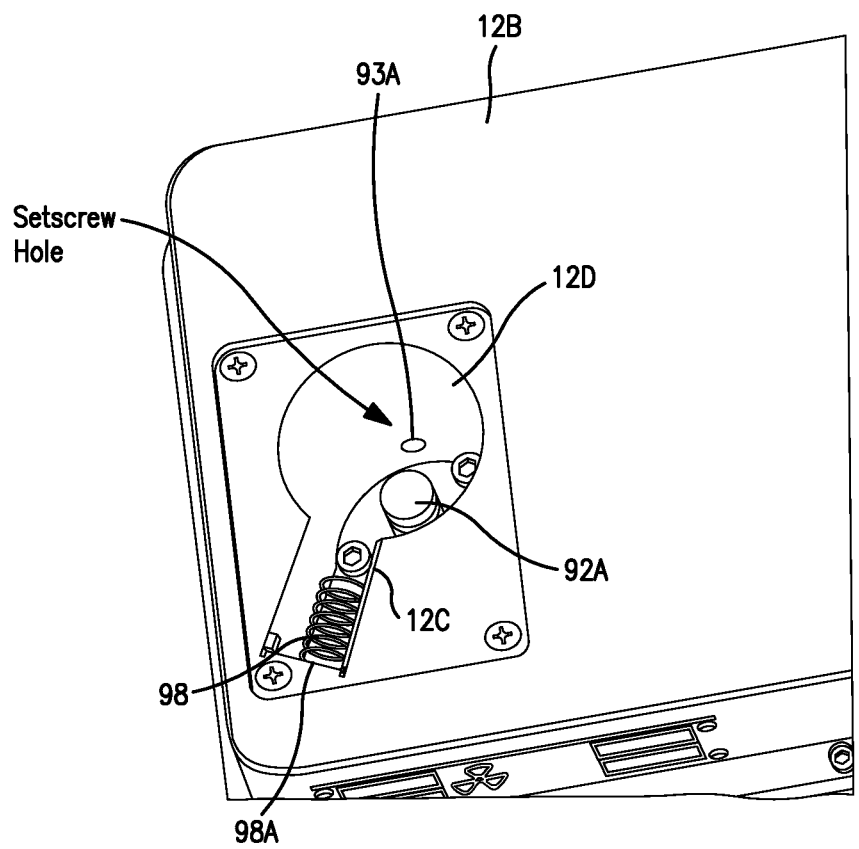
FIGS. 19-24 illustrate partially perspective bottom views of an embodiment of a nuclear gauge and components of a radiation shield assembly according to the present subject matter.

The at least one replaceable sliding guide 140 shown in FIGS. 18A-18C can be or can include a polymer having a low coefficient of friction. The polymer can be at least one of polytetrafluoroethylene, perfluoroalkoxy, and fluorinated ethylene propylene. The at least one replaceable sliding guide 140 can include a body 142 and an arm 144 extending outward from the body 142. The body 142 can include a rectangular shape with a base side 146 and the arm 144 can comprise a different rectangular shape extending from the base side 146, wherein the body 142 has a height $H_B$ that is larger than a height $H_A$ of the arm 144 thereby forming a notch 148 in the at least one replaceable sliding guide 140.

The body 142 of the replaceable sliding guide 140 may extend partially into the safety shield 92 when the replaceable sliding guide 140 is seated in its position. The arm 144 extends further into the safety shield when the replaceable sliding guide 140 is seated in its position. However, in some embodiments, the arm 144 might not extend into the intersection of the shield track segment 92B and the passageway 92A. This configuration can possibly provide greater radiation shielding by not compromising the amount of radiation shielding material in this area of the safety shield 92. The amount of surface area of the body 142 of the replaceable sliding guide 140 as compared to the amount of surface area of the arm 144 of the replaceable sliding guide 140 is importantly balanced between the amount of reduced friction and the protection of the safety shield 92 and track 96 from scarring from the movement of the sliding block 94 as compared to the reduction of radiation shield material provided by the safety shield. The larger the body 142, the more reduced friction and protection of the safety shield 92 and track 96 from scarring is provided. At the same time, more radiation shielding material is removed from the critical juncture between the sliding block 94 and the safety shield 92, especially when close to the intersection of the shield track segment 92B and the passageway 92A. Thus, a safe and effective medium as to the size and shape of the of the replaceable sliding guide 140 can be reached.

For example, the height $H_B$ of the body 142 can range from about three times to about six times the height $H_A$ of the arm 144. For instance, the height $H_B$ of the body can be about six times the height $H_A$ of the arm 144. In one embodiment, the height $H_B$ of the body 142 is about 1.500 inches and the height $H_A$ of the arm 144 is about 0.250 inches.

Similarly, the lengths of the body 142 and the arm 144 of the one or more replaceable sliding guide 140 can be of influence. The body 142 can have a length $L_B$ that is larger than a length $L_A$ of the arm 144. For example, the length $L_B$ of the body 142 can be about two times the length $L_A$ of the arm 144. In one embodiment, the length $L_B$ of the body 142 can be about 1.600 inches and the length $L_A$ of the arm 144 can be about 0.770 inches. Both the body 142 and the arm 144 can have a thickness $W_g$. Thus, the body 142 and the arm 144 can have substantially the same thickness $W_g$. In this manner, the body 142 and the arm 144 of the replaceable sliding guide 140 can provide consistent guidance for the sliding block 94.

The differentiation in height between the body 142 and the arm 144 can also help to reduce the tendency of the replaceable sliding guide 140 to tend to shift or rotate due to the friction contact with the sliding block 94 when the sliding block 94 is moved between its two positions.

The notch 148 created by the body 142 and the arm 144 receives a portion of the safety shield 92 therein as explained below when the replaceable sliding guide 140 is seated in its position. If the arm 144 is of a length and thickness that reduces the opportunity of mechanical failure, then, as the size of the notch area 148 increases, the opportunity of the shifting of the replaceable sliding guide 140 is reduced.

The one or more replaceable sliding guides 140 also provide a dirt trapping function. The one or more replaceable sliding guides 140 can be made of a material that is softer than the hardened metal or rock. Such material, such as the polymers described above, can capture dirt and grit that enter the track 96. Since the dirt and grit that is likely to scar the safety shield are likely harder than the one or more replaceable sliding guides 140, this dirt and grit will likely embed in one or more replaceable sliding guides 140 thereby trapping the dirt and grit therein until the one or more replaceable sliding guides 140 are cleaned or disposed of. Thus, such dirt and grit are kept away from the safety shield 92. The placement of the arms 144 of one or more replaceable sliding guides 140 at the base where dirt and grit enter can provide an early protection of the safety shield by helping to keep the dirt and grit from entering further into the safety shield 92.

Figure 23:
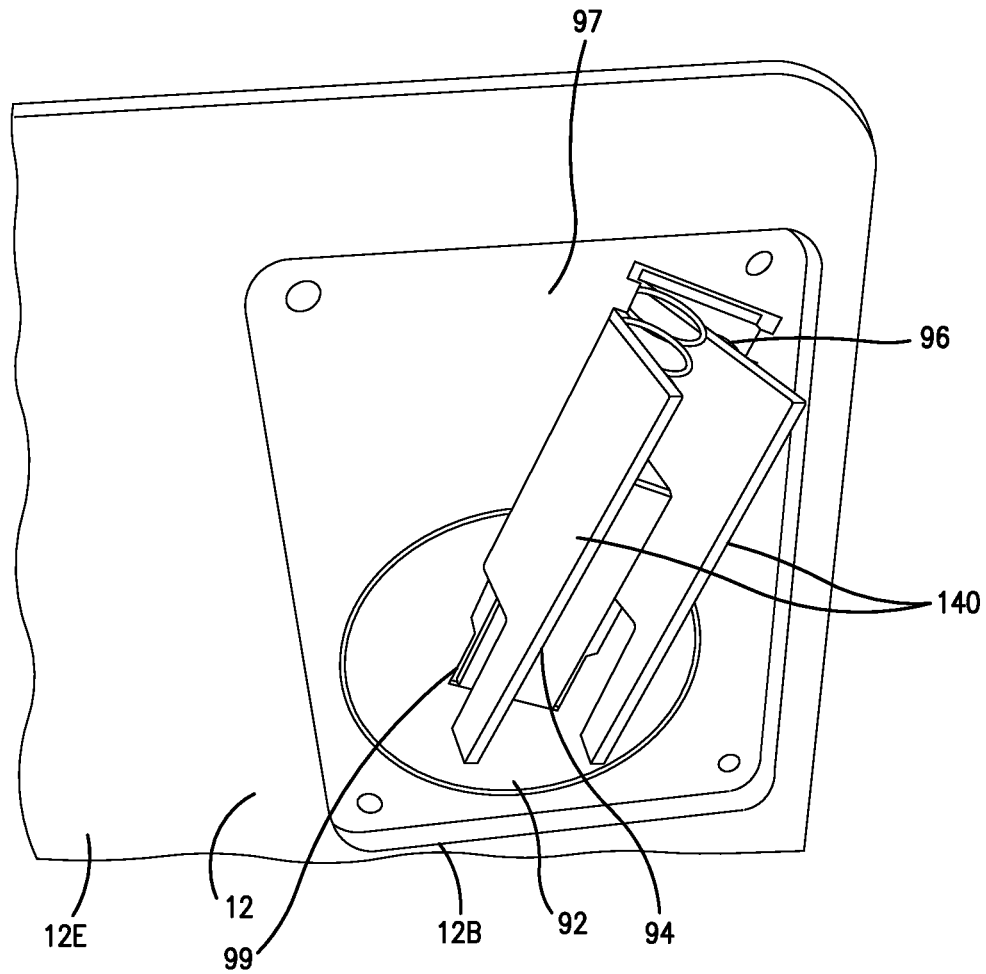

In embodiments of the replaceable sliding guide 140 that have an arm 144, the safety shield 92 can define an indentation 99, as shown in FIGS. 17 and 23, configured to receive the arm 144 of the replaceable sliding guide 140 so that an outer surface 140A of the replaceable sliding guide 140 is about flush with an outer surface of shield track segment 92B of the safety shield 92. The arm 144, by engaging the indentation 99, can reduce the shifting of the sliding guide 140 in the safety shield 92 caused by movement of the sliding block 94. In embodiments where the base 12B of the gauge housing 12 includes a base track segment 12C and the base track segment 12C and the shield track segment 92B are alignable to form the track 96, the base track segment 12C can have a width that is larger than the width of the shield track segment 92B for receiving the body 142 of the at least one replaceable sliding guide 140.

Figure 24:
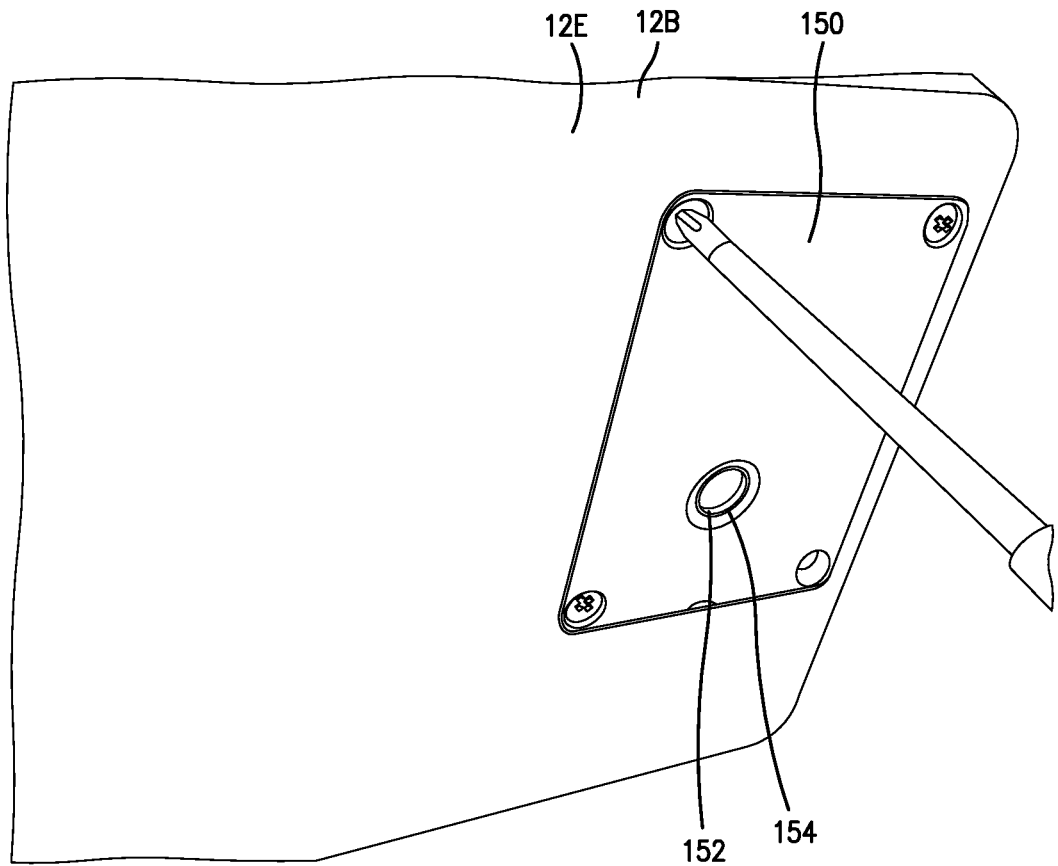
Figure 25A:
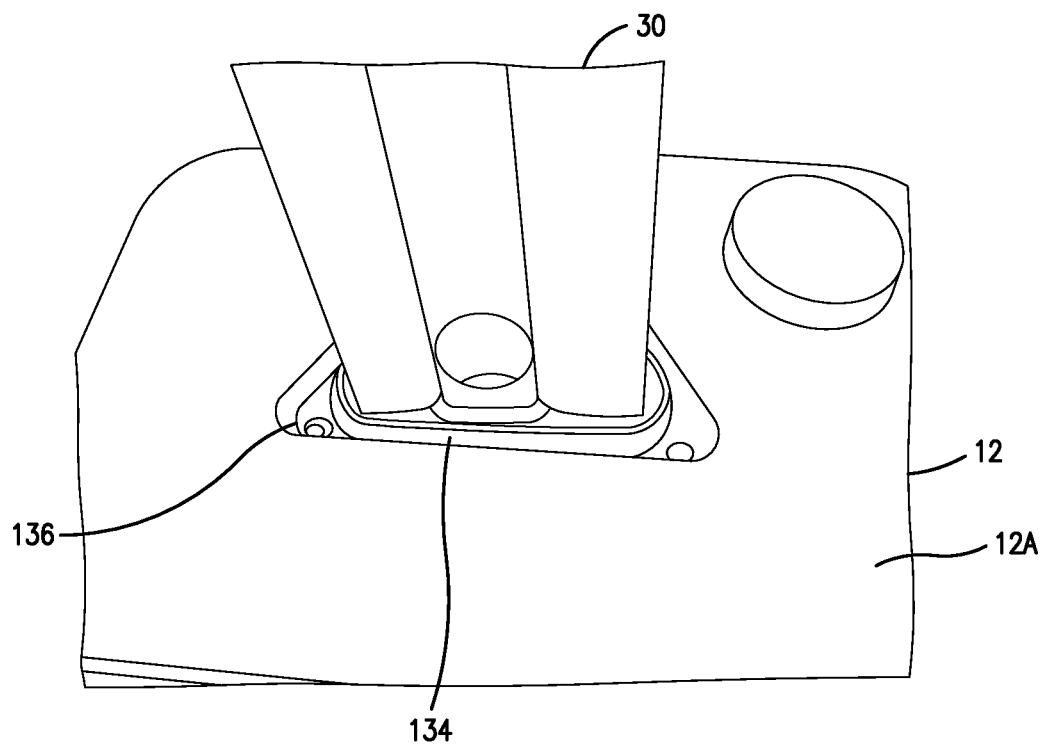
FIGS. 25A-25C illustrate partially perspective views of an embodiment of a nuclear gauge according to the present subject matter.
Figure 25B:
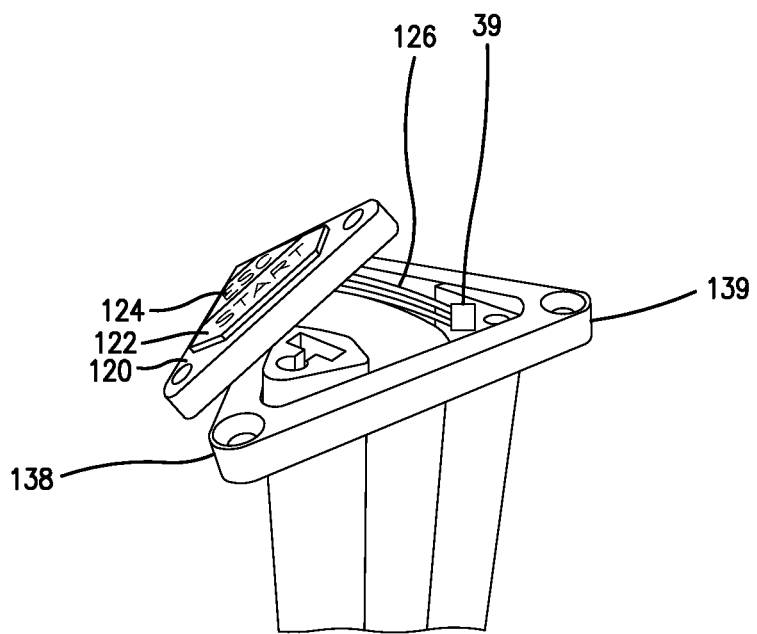
Figure 25C:
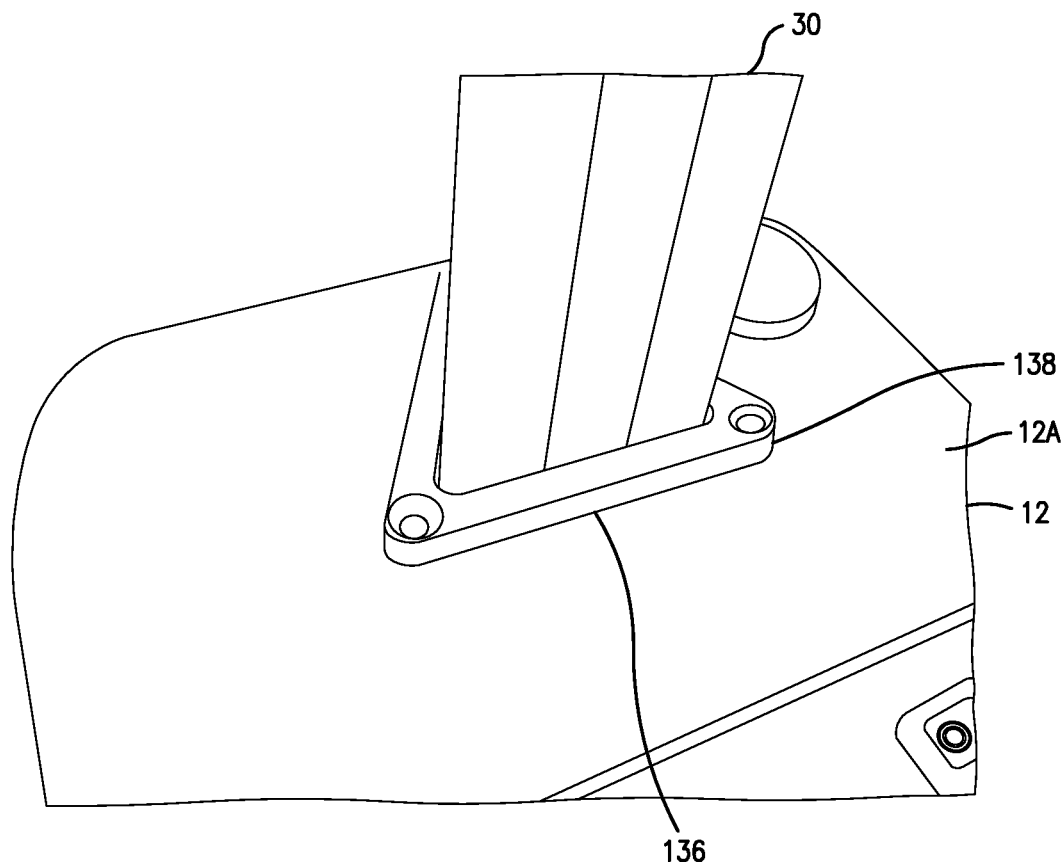

A cover plate 150 for securing the radiation shield assembly 90 within the gauge housing 12 can be included with the radiation shield assembly 90. The cover 150 can be a scraper plate that includes a scraper ring 152. The scraper ring 152 can be held in place in the cover plate 150 by a ring retainer 154 as shown in FIG. 24. The cover plate 150 can be placed in a recess 97 in the lower surface 12E of the base 12B of the gauge housing 12. Once installed, the cover plate 150 can abut the base side 144A of the at least one replaceable sliding guide 140. The outer surface of the cover plate 150 can be flush with the lower surface 12E of the base 12B. The cover plate 150 is positioned on the base 12B at an angle that covers the rest of the radiation shield assembly 90 and such that the entire radiation shield assembly 90 is contained inside the base 12B underneath the cover plate 150. Referring back to the remote keypad 120 as shown in FIGS. 1-3 and 25B, such a keypad 120 located at the end of the tower 30 distal from the gauge housing 12 is intended to reduce the amount of bending and/or stooping required by the operator of the gauge 10. The operator's greatest benefit is gained while using the gauge 10 on an asphalt mat in the backscatter position. The operator will identify a measurement location on the asphalt mat. The operator will then move the source rod 20 to the backscatter position of approximately contacting the surface (the transmission mode assumes a BS position of zero, true that it is about 2 inches from safe position, but safe is not zero). The operator can then, with very little movement, press the start switch 122 to initiate the gauge counting. The location of the remote keypad 120 when located on the end of the tower 30 distal from the gauge housing 12 can be approximately two feet off of the asphalt mat and remains at that distance regardless of the source rod position.

Alternatively, the operator can identify the measurement location, place the source rod 20 in the backscatter position and then press a start switch on the user interface 13 of the gauge 12 located on the gauge housing 12. The location of the user interface 13 on the gauge housing 12 is approximately 5 to 6 inches off of the asphalt mat. Typically, to press the start switch on the user interface 13 located on the gauge housing 12 to initiate a gauge count, the operator will have to bend their back all of the way forward or stoop down closer to the asphalt mat to begin a gauge count. While the use of the remote keypad 120 provides a more ergonomically safe method to operate the gauge 10, either the remote keypad 120 or the user interface 13 on the gauge housing 12 can be used.

Thus, the first and second user interfaces 13 and 120 share some functionality with the first and second user interfaces with each including at least one keypad switch having functionality for communicating the same user input to the nuclear gauge computing system. For example, both the remote keypad 120 and the user interface 13 on the gauge housing can share the "start" and "escape" functions in the embodiment shown, since the remote keypad 120 includes both a start switch 122 and an escape switch 124. Electrically, the start switch 122 and escape switch 124 can be wired in parallel to the same two keys on the user interface 13 located on the gauge housing 12. The firmware operating the gauge 10 can be written in a manner that will allow a single key press of the start switch 122 to begin a gauge count and allow the operator to store that gauge count information in a gauge memory in the CPU 17 with an additional single key press of the start switch 122. Alternatively, an I/O interrupt could be initialed by start switch 122 letting the gauge software enter the requested state, such as starting a count or measurement.

The remote keypad 120 can be located on the stationary support tower 30. This tower 30 provides an excellent location for a stationary keypad and a routing compartment 39 to route electrical wiring 126 from the remote keypad 120 into the gauge housing 12 for connection with the CPU 17. Alternatively, the remote keypad 120 can be located on the handle 50. Because the handle 50 moves with the source rod 20, the power source to operate the remote keypad 120 could be contained within the handle 50. For example, a battery can be provided or power can be established with sliding contacts between the gauge 10 and handle 50.

Further, the keypad 120, as stated above, can be an entity totally separate from the physical body of the gauge 10. For example, the remote keypad 120 can be a fob that may be placed on a lanyard that can be hung around the operator's neck. Methods of communication between the CPU 17 in the gauge housing 12 and the remote keypad 120 for such embodiments where the remote keypad is secured to the handle or the remote keypad as a separate entity can be wireless in nature. For example, a transmitter can be located in the handle and a receiver can be located in the gauge housing for embodiments where the remote keypad is located on the handle. For embodiments where the remote keypad is a separate entity such as a fob, a transmitter can be located in the remote keypad and a receiver can be located in the gauge housing. Methods of wireless communications can be established via infrared or RF, BLUETOOTH®, or the like.

Methods of Assembly

The gauge 10 can be assembled in different ways including the radiation shield assembly 90 and/or related components. The methods of assembling a gauge and its related components set forth below are provided by way of example to illustrate embodiments thereof and are not meant to limit the present subject matter. Other methods of assembling a gauge and its related components can be used without deviating from the scope and spirit of the present subject matter.

As stated above, in the past the safety shields, which protect the user when the radioactive source is in the safe or backscatter position, have been constructed out of tungsten. While lead is a much less expensive radiation shielding material, it is generally too soft and wears out too quickly when used in such shielding operations within a nuclear gauge. To traverse these obstacles, the surface of a lead safety shield 92 can be hardened to reduce wear, while still providing all the shielding benefits without this excessive wear. This hardening of the surface of the lead safety shield 92 can be accomplished by any method including molding in wear plates in strategic locations in the lead safety shield 92 itself. Further, the safety shield 92 can be coated or surrounded with a hard surface material that increases the durability of the lead.

In addition to avoiding wear in some locations, it is desirable to allow the sliding of two components. For example, the sliding block 94 slides back and forth as described above to close the vertical conduit 32 in which the source rod 20 resides. By adding material in the correct location, the friction between these two components can be kept low and dirt resistance kept high. The replaceable sliding guides 140 can help accomplish this.

Figure 20:
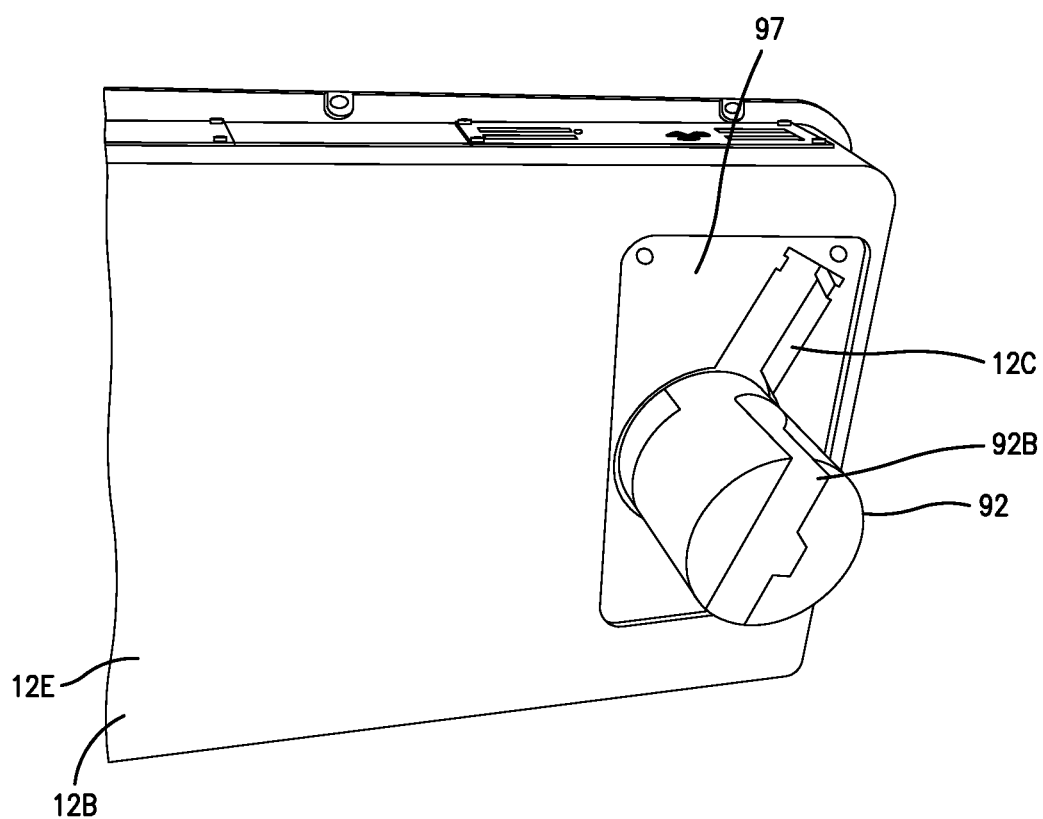

To assemble the gauge 10, the radiation shield assembly 90 can be put together within the base 12B of the gauge housing 12. The safety shield 90 can be inserted into the cavity created by the shield housing 12D in the base 12B of the gauge housing 12 as shown in FIG. 20. Note the shield track segment 92B should be aligned with base track segment 12C. When the safety shield 92 is fully inserted into the base 12B, the top of the safety shield 92 can be, for example, no higher than the recess 97 in the base 12B that receives the cover plate 150 as shown in FIGS. 21-23. For instance, the safety shield 92 can be flush with the base 12B.

While the safety shield 92 is pressed inside the base 12B, the base 12B and the safety shield 92 can be held in place as one or more set screws 93 can be screwed into the corresponding screw holes 93A in the shield housing 12D. For example, two set screws 93 can be screwed into properly spaced screw holes 93A to hold the safety shield 92 in place. In one embodiment, only about ½ to about ¾ of a rotation after a set screw 93 makes contact with the safety shield 92 can create enough friction to hold the safety shield 92 in place.

The shield spring 98 can be inserted into the sliding block 94. For example, the spring 98 can be inserted into an aperture in the end 94B of the sliding block 94. Lubricant can be applied to the sliding block 94 on the sides that contact the replaceable sliding guide 140 and the side walls of the safety shield that form the shield track segment 92B. The other end of the spring 98 can then be inserted into the spring guide 98A. At this point, the sliding block 94, spring 98 and spring guide 98A form a sliding block assembly. The sliding block 94, spring 98 and spring guide 98A can then be inserted into the track 96.

The replaceable sliding guides 140 can be inserted on either side of the sliding block 94 between the sliding block 94 and the track 96 as shown in FIG. 23. The bodies 142 of the replaceable sliding guides 140 can reside mainly in the base track segment 12C, and the arms 144 of the replaceable sliding guides 140 can reside in the shield track segment 92B. The replaceable sliding guides 140 can be inserted into cavities in the track 96 such that the outer surface of the replaceable sliding guides 140 are flush with the outer walls of the track 96 and not covered by the replaceable sliding guides 140. When fully inserted, the two replaceable sliding guides 140 can be secured in place in their machined cutout in the track 96, thereby allowing the sliding block 94 to easily slide. For example, the arm 144 of the replaceable sliding guides 140 can reside in indentations 99 in the safety shield 92 (see FIG. 23).

To create a scraper plate that scrapes dirt and grit off the source rod 20, a scraper ring 152 can be inserted into the cover plate 150 (See FIG. 24). A ring retainer 154 can be inserted into the cover plate 150 to secure the scraper ring 152. Lubrication can be applied to the cover plate 150 where the sliding block will move when operating the source rod 20. The cover plate 150 can be installed on the base 12B of the gauge housing 12. The cover plate 150 can be placed in the recess 97 and screwed into place as shown in FIG. 24. The cover plate 150 is positioned on the base 12B at an angle such that the rest of the radiation shield assembly 90 is contained inside the base 12B and underneath the cover plate 150.

If the sliding block 94 is not kept clean, it can stick partially or completely open when the source rod 20 is raised to the safe (shielded) position as shown in FIG. 2. This sticking will result in high radiation levels near or in line with the source rod opening on the bottom of the gauge. After cleaning and reassembling the gauge 10 as described below, the operation of the sliding block 94 can be checked by pushing the source rod 20 into the backscatter position, then returning it to the safe position. A click audible enough to be heard should be made as the sliding block 94 snaps shut. The opening at the scraper ring 152 at the base 12B of the gauge housing 12 can be inspected to confirm that the sliding block 94 is closed. If not, the sliding block spring 98 can be checked to confirm that it was properly installed after cleaning. In another embodiment, sensors can provide detection of a properly closed sliding block 94 in the safety shield 92, alerting the user with an alarm or message in the event that the sliding block 94 does not close.

The sliding block 94 may require cleaning if the source rod 20 becomes difficult to lower into a "measure" position, or if a click is not heard when the source rod 20 is raised to the safe position the as shown in FIG. 2. An improperly operating sliding block 94 may also result in erratic or incorrect standard measurements and density readings and can also result in increased radiation levels.

With the source rod 20 in the safe position as shown in FIG. 2, the gauge 10 can be placed on its side. The heads of the four corner screws that hold the cover plate 150 to the gauge housing base 12B can be cleaned (FIG. 24). The four screws in the corner of the cover plate 150 can be removed and the cover plate 150 can be removed from the recess 97 in the base 12B. To reduce radiological exposure, the operator should stand to one side of the gauge 10. Paying close attention to the position of the sliding block 94, the block 94 can be removed. If necessary, the replaceable sliding guides 140 can also be removed and cleaned or replaced. The sliding block 94 and the cavity can be cleaned. For example, a stiff brush or rag soaked in solvent can be used to clean the sliding block 94 and the cavity. The sliding block 94 with the angled side up can be reinstalled. A coating of lubricant can be applied to the top angled surface of the sliding block 94. If removed, new or cleaned replaceable sliding guides 140 can be reinstalled. Then, the cover plate 150 can be reinstalled. When installing the cover plate 150, the screws should not be over-tightened to ensure that the source rod 20 and sliding block 94 move freely.

Embodiments of the present disclosure shown in the drawings and described above are exemplary of numerous embodiments that can be made within the scope of the appending claims. It is contemplated that the configurations of nuclear gauges, their components and the methods of assembling the same can comprise numerous configurations other than those specifically disclosed. The scope of a patent issuing from this disclosure will be defined by these appending claims.

What is claimed is:

1. A nuclear gauge, comprising:
   a gauge housing having a vertical cavity therethrough and a base, the base including a base track portion disposed therein;
   at least one radiation detector located within the housing and adjacent to the base of the housing;
   a vertically moveable source rod extending into the cavity of the gauge housing;
   a radiation source operatively positioned within a distal end of the source rod, the source rod being vertically extendable and retractable to a plurality of predetermined source rod positions so as to change the spatial relationship between the radiation source and the at least one radiation detector; and
   a radiation shield assembly comprising:
      a sliding block positionable to move laterally between two positions, a first position blocking a distal end of the vertical cavity of the gauge housing such that radiation is shielded from exiting the cavity and a second position adjacent to the vertical cavity and allowing vertical movement through the radiation shield assembly;
      a track configured to receive the sliding block and guide movement of the sliding block;
      a spring engaging the sliding block and biasing the sliding block into the first position;
      a safety shield, the safety shield including a shield track segment therein that comprises at least a portion of the track;
      and
      at least one replaceable sliding guide positionable within the track adjacent the sliding block, the at least one replaceable sliding guide configured to reduce friction as the sliding block moves between the first position and the second position, wherein the at least one sliding guide is insertable into at least one cavity in the track such that an outer surface of the at least one sliding guide is flush with at least one outer wall of the track.

2. A nuclear gauge according to claim 1, wherein the base of the gauge housing includes a base track segment, the base track segment and the shield track segment being alignable to form the track.

3. A nuclear gauge according to claim 2, wherein the at least one replaceable sliding guide comprises two replaceable sliding guides with each replaceable sliding guide extending over at least a portion of the base track segment and the shield track segment on opposing walls of the track.

4. A nuclear gauge according to claim 1, wherein the track is configured to extend in a direction within the nuclear gauge so that as the sliding block moves from the first position to the second position, the sliding block moves away from the at least one radiation detector.

5. A nuclear gauge according to claim 4, wherein the track extends at an angle of between about 90° and about 180° as measured from a plane extending between the at least one radiation detector and the point of the track closest to the at least one radiation detector.

6. A nuclear gauge according to claim 5, wherein the track extends at an angle of between about 100° and about 135°.

7. A nuclear gauge according to claim 5, wherein the angle of the track biases the sliding block toward a closed position through gravity when placed in a carrying case and the carrying case is in its standard upright position.

8. A nuclear gauge according to claim 1, wherein the safety shield comprises lead.

9. A nuclear gauge according to claim 8, wherein the safety shield includes inserts of a hard surface material.

10. A nuclear gauge according to claim 9, wherein the hard surface material comprises at least one of steel, hardened steel, high carbon steel, stainless steel, or tungsten.

11. A nuclear gauge, comprising:
   a gauge housing having a vertical cavity therethrough and a base, the base including a base track portion disposed therein;
   at least one radiation detector located within the housing and adjacent to the base of the housing;
   a vertically moveable source rod extending into the cavity of the gauge housing;
   a radiation source operatively positioned within a distal end of the source rod, the source rod being vertically extendable and retractable to a plurality of predetermined source rod positions so as to change the spatial relationship between the radiation source and the at least one radiation detector;
   a radiation shield assembly comprising:
      a sliding block positionable to move laterally between two positions, a first position blocking a distal end of the vertical cavity of the gauge housing such that radiation is shielded from exiting the cavity and a second position adjacent to the vertical cavity and allowing vertical movement through the radiation shield assembly;
      a track configured to receive the sliding block and guide movement of the sliding block;
      a spring engaging the sliding block and biasing the sliding block into the first position;
      a safety shield, the safety shield including a shield track segment therein that comprises at least a portion of the track;
      and
      at least one replaceable sliding guide positionable within the track adjacent the sliding block, the at least one replaceable sliding guide configured to reduce friction as the sliding block moves between the first position and the second position;

wherein the safety shield comprises lead; and wherein the shield track segment includes two opposing side walls extending into the safety shield and an end wall disposed between the side walls within the safety shield with at least a portion of the end wall within the safety shield comprising a hard surface material.

12. A nuclear gauge according to claim 11, wherein the hard surface material comprises at least one of steel, hardened steel, high carbon steel, stainless steel, or tungsten.

13. A nuclear gauge according to claim 1, wherein the safety shield comprises a molded block.

14. A nuclear gauge according to claim 1, wherein the at least one replaceable sliding guide comprises a polymer having a low coefficient of friction.

15. A nuclear gauge according to claim 14, wherein the polymer comprises at least one of polytetrafluoroethylene, perfluoroalkoxy, and fluorinated ethylene propylene.

16. A nuclear gauge according to claim 1, wherein the at least one replaceable sliding guide comprises a body and an arm extending outward from the body.

17. A nuclear gauge according to claim 16, wherein the body comprises a rectangular shape with a base side and the arm comprises a rectangular shape extending from the base side, the body having a height that is larger than a height of the arm thereby forming a notch in the at least one replaceable sliding guide.

18. A nuclear gauge according to claim 17, wherein the safety shield defines an indentation configured to receive the arm of the at least one replaceable sliding guide so that an outer surface of the at least one replaceable sliding guide is about flush with an outer surface of shield track segment of the safety shield.

19. A nuclear gauge according to claim 18, wherein the base of the gauge housing includes a base track segment, the base track segment and the shield track segment being alignable to form the track, the base track segment having a width that is larger than the width of the shield track segment for receiving the body of the at least one replaceable sliding guide.

20. A nuclear gauge according to claim 16, further comprising a scraper plate for securing the radiation shield assembly within the gauge housing, the scraper plate abutting the base side of the at least one replaceable sliding guide.

21. A nuclear gauge, comprising:
- a gauge housing having a vertical cavity therethrough and a base, the base including a base track portion disposed therein;
- at least one radiation detector located within the housing and adjacent to the base of the housing;
- a vertically moveable source rod extending into the cavity of the gauge housing;
- a radiation source operatively positioned within a distal end of the source rod, the source rod being vertically extendable and retractable to a plurality of predetermined source rod positions so as to change the spatial relationship between the radiation source and the at least one radiation detector;
- a radiation shield assembly comprising:
  - a sliding block positionable to move laterally between two positions, a first position blocking a distal end of the vertical cavity of the gauge housing such that radiation is shielded from exiting the cavity and a second position adjacent to the vertical cavity and allowing vertical movement through the radiation shield assembly;
  - a track configured to receive the sliding block and guide movement of the sliding block;
  - a spring engaging the sliding block and biasing the sliding block into the first position;
  - a safety shield, the safety shield including a shield track segment therein that comprises at least a portion of the track; and
  - at least one replaceable sliding guide positionable within the track adjacent the sliding block, the at least one replaceable sliding guide configured to reduce friction as the sliding block moves between the first position and the second position;
- wherein the at least one replaceable sliding guide comprises a body and an arm extending outward from the body; and
- wherein the safety shield includes a passageway through which the source rod is configured to pass, the passageway intersecting the shield track segment and wherein the at least one replaceable sliding guide comprises a size and shape so that when installed in the safety shield, the arm of the at least one replaceable sliding guide does not extend into an intersection of the passageway and the shield track segment.

22. The nuclear gauge of claim 1, wherein the nuclear gauge is a density gauge, a bulk density gauge, a thin overlay gauge, a thin layer gauge, or a combination thereof.

23. The nuclear gauge of claim 1, wherein the at least one radiation detector comprises at least one set of Gieger-Muller tubes.

24. A radiation shield assembly for use in a nuclear gauge, the radiation shield assembly comprising:
- a sliding block positionable to move laterally between a closed position and an open position;
- a track configured to receive the sliding block and guide movement of the sliding block;
- a spring engaging the sliding block and biasing the sliding block into the closed position;
- a safety shield including a shield track segment therein that comprises at least a portion of the track; and
- at least one replaceable sliding guide positionable within the track adjacent the sliding block, the at least one replaceable sliding guide configured to reduce friction as the sliding block moves between the closed position and the open position, wherein the at least one replaceable sliding guide is insertable into at least one cavity in the track such that an outer surface of the at least one sliding guide is flush with at least one outer wall of the track.

25. A radiation shield assembly according to claim 24, wherein the safety shield comprises lead.

26. A radiation shield assembly according to claim 25, wherein the safety shield includes inserts of a hard surface material.

27. A radiation shield assembly according to claim 26, wherein the hard surface material comprises at least one of steel, hardened steel, high carbon steel, stainless steel, or tungsten.

28. A radiation shield assembly for use in a nuclear gauge, the radiation shield assembly comprising:
- a sliding block positionable to move laterally between a closed position and an open position;
- a track configured to receive the sliding block and guide movement of the sliding block;
- a spring engaging the sliding block and biasing the sliding block into the first position;
- a safety shield including a shield track segment therein that comprises at least a portion of the track; and at least one replaceable sliding guide positionable within the track adjacent the sliding block, the at least one replaceable sliding guide configured to reduce friction as the sliding block moves between the closed position and the open position;

wherein the safety shield comprises lead; and wherein the shield track segment includes two opposing side walls extending into the safety shield and an end wall disposed between the side walls within the safety shield with at least a portion of the end wall within the safety shield comprising a hard surface material.

29. A radiation shield assembly according to claim 28, wherein the hard surface material comprises at least one of steel, hardened steel, high carbon steel, stainless steel, or tungsten.

30. A radiation shield assembly according to claim 24, wherein the safety shield comprises a molded block.

31. A radiation shield assembly according to claim 24, wherein the at least one replaceable sliding guide comprises a polymer having a low coefficient of friction.

32. A radiation shield assembly according to claim 31, wherein the polymer comprises at least one of polytetrafluoroethylene, perfluoroalkoxy, and fluorinated ethylene propylene.

33. A radiation shield assembly according to claim 24, wherein the at least one replaceable sliding guide comprises a body and an arm extending outward from the body.

34. A radiation shield assembly according to claim 33, wherein the body comprises a rectangular shape with a base side and the arm comprises a rectangular shape extending from the base side, the body having a height that is larger than a height of the arm thereby forming a notch in the at least one replaceable sliding guide.

35. A radiation shield assembly according to claim 34, wherein the safety shield defines an indentation configured to receive the arm of the at least one replaceable sliding guide so that an outer surface of the at least one replaceable sliding guide is about flush with an outer surface of shield track segment of the safety shield.

36. A radiation shield assembly according to claim 35, wherein the base of the gauge housing includes a base track segment, the base track segment and the shield track segment being alignable to form the track, the base track segment having a width that is larger than the width of the shield track segment fiving the body of the at least one replaceable sliding guide.

37. A radiation shield assembly according to claim 33, further comprising a scraper plate for securing the radiation shield assembly within the gauge housing, the scraper plate abutting the base side of the at least one replaceable sliding guide.

38. A replaceable sliding guide for use in a radiation shield assembly of a nuclear gauge, the replaceable sliding guide comprising a body having a rectangular shape with a base side and an arm having a rectangular shape extending from the base side, the body having a height that is larger than a height of the arm thereby forming a notch in the replaceable sliding guide, the replaceable sliding guide being positionable within a track adjacent to a sliding block, and the replaceable sliding guide being configured to reduce friction as the sliding block moves between a first position of the track and a second position, wherein the replaceable sliding guide is insertable into at least one cavity in the track such that an outer surface of the replaceable sliding guide is flush with at least one outer wall of the track.

39. A replaceable sliding guide according to claim 38, wherein the replaceable sliding guide comprises a polymer having a low coefficient of friction.

40. A replaceable sliding guide according to claim 39, wherein the polymer comprises at least one of polytetrafluoroethylene, perfluoroalkoxy, and fluorinated ethylene propylene.

41. A replaceable sliding guide according to claim 38, wherein the height of the body is between about three times to about six times the height of the arm.

42. A replaceable sliding guide according to claim 38, wherein the height of the body is about 1.500 inches and the height of the arm is about 0.250 inches.

43. A replaceable sliding guide according to claim 38, wherein the body has a length that is larger than a length of the arm.

44. A replaceable sliding guide according to claim 38, wherein the length of the body is about two times the length of the arm.

45. A replaceable sliding guide according to claim 44, wherein the length of the body is about 1.600 inches and the length of the arm is about 0.770 inches.

46. A replaceable sliding guide according to claim 38, wherein the body and the arm have substantially the same width.

* * * * *